United States Patent
Kumar et al.

(10) Patent No.: US 9,005,607 B2
(45) Date of Patent: Apr. 14, 2015

(54) STEM CELL CULTURE METHOD

(71) Applicant: Keele University, Staffordshire (GB)

(72) Inventors: Deepak Kumar, Staffordshire (GB); Ying Yang, Staffordshire (GB); Nicholas Forsyth, Staffordshire (GB)

(73) Assignee: Keele University, Keele, Staffordshire (GB)

( * ) Notice: Subject to any disclaimer, the term of this patent is extended or adjusted under 35 U.S.C. 154(b) by 0 days.

(21) Appl. No.: 13/800,325

(22) Filed: Mar. 13, 2013

(65) Prior Publication Data

US 2014/0050704 A1 Feb. 20, 2014

(30) Foreign Application Priority Data

Aug. 17, 2012 (GB) .................................. 1214704.7

(51) Int. Cl.
*C12N 5/0735* (2010.01)
*A61L 27/38* (2006.01)
*A61L 27/18* (2006.01)
*A61L 27/56* (2006.01)

(52) U.S. Cl.
CPC .......... *C12N 5/0606* (2013.01); *C12N 2500/02* (2013.01); *C12N 2533/40* (2013.01); *C12N 2533/90* (2013.01); *A61L 27/3834* (2013.01); *C12N 2533/30* (2013.01); *A61L 27/18* (2013.01); *A61L 27/3895* (2013.01); *A61L 27/56* (2013.01); *A61L 2400/12* (2013.01)

(58) Field of Classification Search
CPC ........... C12N 2500/02; C12N 2533/90; C12N 5/0606
See application file for complete search history.

(56) References Cited

U.S. PATENT DOCUMENTS

| | | |
|---|---|---|
| 6,184,035 B1 | 2/2001 | Csete et al. |
| 2004/0224401 A1 | 11/2004 | Ludwig et al. |
| 2009/0163936 A1 | 6/2009 | Yang et al. |
| 2009/0269845 A1 | 10/2009 | Rezania |
| 2010/0124783 A1 | 5/2010 | Chen et al. |
| 2010/0298937 A1 | 11/2010 | Laurencin et al. |
| 2011/0033928 A1 | 2/2011 | Smith et al. |

FOREIGN PATENT DOCUMENTS

| | | |
|---|---|---|
| WO | WO 2006/019366 | 2/2006 |
| WO | WO 2006/033103 | 3/2006 |
| WO | WO 2006/053378 | 5/2006 |
| WO | WO 2009/133059 | 11/2009 |
| WO | WO 2010/059778 | 5/2010 |
| WO | WO 2010/115187 | 10/2010 |
| WO | WO 2011/142832 | 11/2011 |

OTHER PUBLICATIONS

Yao et al. (PNAS 2006; 103(18): 6907-6912).*
Gauthaman et al. (J. Cell. Mol. Med. 2009; 13(9B): 3475-3484).*
Wimpenny et al. (Tissue Engineering: Part C; 2010: 16(3): 503-509).*
Ouyang et al. (Expert Opin. Biol. Ther. 2008; 8(7): 895-909).*
Venugopal et al (J. Biomed Mater Res Part B: Appli Biomater. 2007; 84B: 34-48).*
Ted Andrews (Biotechniques Protocol Guide. 2009; p. 15).*
Carlberg et al. "Electrospun polyurethane scaffolds for proliferation and neuronal differentiation of human embryonic stem cells" Biomed. Mater. 4:1-7 (2009).
Gauthaman et al. "Nanofibrous substrates support colony formation and maintain stemness of human embryonic stem cells" J. Cell. Mol. Med. 13(9B):3475-3484 (2009).
Liu et al. "Chemically-defined scaffolds created with electrospun synthetic nanofibers to maintain mouse embryonic stem cell culture under feeder-free conditions" Biotechnol Lett. 34(10):1951-1957(Oct. 2012) DOI 10.1007/s10529-012-0973-9.
Liu et al. "Growth and Attachment of Embryonic Stem Cell Colonies on Single Nanofibers" Micro and Nanosystems, 2:269-273 (2010).
Ludwig et al. "Derivation of human embryonic stem cells in defined conditions" Nature Biotechnology. 24(2);185-187 (Feb. 2006).
Ramirez et al. "Effect of long-term culture of mouse embryonic stem cells under low oxygen concentration as well as on glycosaminoglycan hyaluronan on cell proliferation and differentiation" Cell Prolif. 44:75-85 (2011).
Shabani et al. "Improved infiltration of stem cells on electrospun nanofibers" Biochemical and Biophysical Research Communications 382:129-133 ((2009)).
Ulloa-Montoya et al. "Culture Systems for Pluripotent Stem Cells" Journal of Bioscience and Bioengineering100(1):12-27 (2005).
Westfall "Identification of Oxygen-Sensitive Transcriptional Programs in Human Embryonic Stem Cells" Stem Cells and Development 17:869-882 (2008).
Wimpenny et al. "One-Step Recovery of Marrow Stromal Cells on Nanofibers" Tissue Engineering: Part C 15(00):1-7 (2009).
Xie et al. "The differentiation of embryonic stem cells seeded on electrospun nanofibers into neural lineages" Biomaterials 30:354-362 ((2009).
Xu et al. "Feeder-free growth of undifferentiated human embryonic stem cells" Nature Biotechnology 19:971-974 (Oct. 2001).
International Search Report and Written Opinion prepared by the European Patent Office for PCT/GB2013/051902 mailed Mar. 21, 2014, 16 pages.

* cited by examiner

*Primary Examiner* — Scott Long

(74) *Attorney, Agent, or Firm* — Swanson & Bratschun, L.L.C.

(57) ABSTRACT

Methods for culturing pluripotent stem cells on fiber scaffolds are provided which result in the expansion of the number of stem cells without loss of pluripotency. Cells obtained by such methods, implants containing such cells and medical methods using such cells are also disclosed.

17 Claims, 9 Drawing Sheets

STEM CELL CULTURE METHOD

RELATED APPLICATION

The instant application claims priority to GB Application No. 1214704.7, filed Aug. 17, 2012; which is incorporated herein by reference in its entirety.

FIELD OF THE INVENTION

The present invention relates to methods for culturing stem cells and particularly to methods of culturing pluripotent stem cells.

BACKGROUND TO THE INVENTION

Interest in stem cell biology and its association with tissue engineering and regenerative medicine has grown rapidly over the past decade. Autologous, adult and cord-derived stem cells were the first to be implanted into patients for numerous purposes including haematological, musculoskeletal, and immunological disorders [1]. More recently, hESCs have also been approved for clinical trials in both macular degeneration and spinal cord injury, though we can anticipate that this list will grow over the coming years [2, 3]. Particular attention has been drawn towards hESC due to their pluripotentiality, immortality, and immunologically privileged nature [4]. These characteristics endow great potential as an off-the-shelf, allogeneic, scalable solution to numerous conditions, for which, adult and cord-derived stem cells are not applicable, due to limited differentiation and/or proliferative capacities [5].

Current methodology for expansion of hESCs is largely reliant on either the mitotically-inactivated feeder cell method (using direct co-culture with embryonic or adult fibroblasts), or the feeder-free method, which utilises feeder cell, pre-conditioned media and a biological substrate, such as Matrigel™ [4, 6]. Unlike with MSC culture, the presence of a feeder cell layer, Matrigel™ or other extracellular matrix component scaffold is considered essential for the culture of ESCs (see Ramirez et al., 2011), with "naked" or uncoated plastic being reportedly unable to support undifferentiated culture of hESCs (Xu et al Nature Biotechnology 2001), whereas mESC culture requires only a thin layer of collagen for self-renewal.

Fok and Zandstra (2005) described stirred-suspension culture systems for the propagation of undifferentiated mouse embryonic stem cells (mESCs). The stirred-suspension culture systems comprised microcarrier and aggregate cultures. Mouse embryonic stem cells cultured on glass microcarriers had population doubling times comparable to tissue-culture flask controls. Upon removal of leukemia inhibitory factor, the mESC aggregates developed into embryoid bodies (EBs) capable of multilineage differentiation. However, LIF does not have this effect on hESC culture (Smith et al, Nature (1988) 336: 688-690). Suspension cultures of mouse ESCs are also described in King and Miller (2005). However, King and Miller (2005) state that "expansion of undifferentiated human ESCs (hESCs) is more difficult than for mESCs and has not yet been reported in stirred cultures".

Matrigel™ itself is a loosely defined substrate, which consists of extracellular matrix proteins from Engelbreth-Holm-Swarm tumours [6]. The inherent limitation of the Matrigel™-based feeder-free method is that it is unsuitable for incorporation into hESC-based clinical trials due to the risk of xenocontamination. In addition, Matrigel™ limits hESC expansion to a two dimensional (2D) environment with subsequent interventions required prior to transplantation. Hence, innovative and novel tissue engineering strategies are urgently required to provide the opportunity of incorporating hESCs with synthetic, biomimetic substrates (scaffolds), with the potential to act as three dimensional (3D) carriers to facilitate ready transplantation into in vivo target sites. Other extracellular matrix components used as a support for stem cell proliferation include laminin, vitronectin, fibronectin, hyaluronan and collagen, or mixtures of these components (see, for example, Ludwig et al., (2006) Nature Biotech 24(2): 185-87), Ramirez et al, 2011). Such mixtures are often only loosely defined in terms of their composition.

Cells are sensitive to nano-scale topography [7]. A common method used for fabricating nano-scale tissue engineering scaffolds is electrospinning. Electrospinning offers advantages over other nanofiber fabrication techniques such as phase separation, self assembly, and template synthesis, as it is fast, efficient, versatile and economical [8, 9]. Electrospinning provides the opportunity to produce nanofibrous scaffolds, of tailored dimensions, that are able to mimic the nano-architecture of native extracellular matrix [10]. Nanofibers also provide a high surface area to volume ratio and high surface roughness resulting in an effective environment for cell adhesion due to increased focal adhesion contact between the cells and the surrounding fibers [11-13]. This is an indication of effective interaction between the cell and the surrounding artificial ECM, which results in the potential transmission of guidance cues to the cells. Electrospun fiber meshes generally have poor mechanical strength, but are highly flexible, which can result in an environment where cells produce fewer stress fibers [14]. An involvement of nanotopographical features in the maintenance of undifferentiated ESCs has been previously proposed [15].

Electrospinning has proven to be of great interest in the field of tissue engineering [16, 17]. It permits fabrication of fibers in both random and aligned conformations, which can be applied to various surfaces and provides the opportunity to use natural or synthetic polymers [18]. Modulation of voltage, electrode-collector distance and polymer concentration allows control of fiber diameter, morphology and porosity of a scaffold/substrate [19].

Previous reports have detailed the biocompatibility of electrospun nanofiber scaffolds to support the attachment, proliferation and differentiation of human bone marrow-derived mesenchymal stem cells (hMSC), cord blood-derived somatic stem cells, neural stem cells, and haematopoietic stem cells [13, 20-27]. Many of these researchers used synthetic polymers such as poly-ε-caprolactone (PCL), poly-L-lactide acid (PLLA), poly(lactic-co-glycolic acid) (PLGA), as they are FDA approved and their bulk degradation properties are well characterised [19]. hMSC was reported to form both osteogenic and chondrogenic lineages on randomly arranged PCL nanofiber scaffolds [20, 28]. In addition, neural stem cells were capable of differentiating into functional nerve cells with increased neurite outgrowth and reduced branching on PCL and collagen/PCL aligned nanofiber scaffolds [20, 23, 28]. Cord blood-derived somatic stem cells, on the other hand, were differentiated towards hepatocyte-like cells on random PCL nanofibers. Albumin, glycogen storage, and α-fetoprotein were all detected after six weeks of differentiation towards a hepatic lineage and RT-PCR analysis showed the presence of endodermal, hepatic genes [25]. These observations were recently expanded; aligned and random nanofiber scaffolds, fabricated using PCL, PLGA and poly-L/D-lactide acid (PLDLA), were demonstrated to being suitable for the isolation and expansion of hMSC directly from bone marrow aspirate while maintaining their multipotent state [27]. However, different types of stem cell may require different cultivation conditions, even if isolated from the same tissue (see Ulloa-Montoya et al., 2005), and so methods for the culture of MSCs are not directly transferrable to ESC or other types of stem cell. Currently, the literature regarding culture and differentiation of hESCs on electrospun fibers is limited. However, murine ESC differentiation into mature neural cells was achieved using retinoic acid, via an embryoid body (EB) stage, when cultured on electrospun, oriented PCL nanofiber scaffolds [29]. Immunostaining was performed to characterise the mature neural cells lineages, including neurons (Tuj-1), oligodendrocytes (O4) and astrocytes (glia fibrillar acidic protein; GFAP). Results showed that culture of EBs on nanofibers (both random and aligned) significantly enhanced the differentiation towards neural lineages. Culture of EBs on oriented nanofibers also significantly enhanced neurite outgrowth when compared to EBs cultured on random nanofibers [29]. Electrospun polyurethane porous nanofibers are described as supporting the proliferation and neuronal differentiation of hESC in previous studies [30]. In this instance, hESC were differentiated towards a neural lineage, as characterised by immunohistochemistry for MAP2, β-tubulin III, and tyrosine hydroxylase (TH). Lineage specificity was demonstrated by the relative absence of GFAP (astrocytes), and a negative immunoreaction for hESC markers Oct-4, Sox2 and Nestin indicated the absence of undifferentiated hESCs. Culture of hESC on electrospun nanofiber substrates fabricated from PCL/collagen and PCL/gelatin has also been described. However, hESC/mouse embryonic fibroblast (MEF) co-culture was the only method by which hESCs could be expanded in a pluripotent state [31].

There thus exists a need in the art to expand pluripotent stem cells such as hESC, in which pluripotency is maintained and which is free of xenocontaminants.

SUMMARY OF THE INVENTION

The invention provides a method of culturing pluripotent stem cells whilst maintaining stemness, the method comprising seeding the pluripotent stem cells onto a fiber scaffold and incubating the pluripotent stem cell loaded fiber scaffold in a gas atmosphere in which the percentage of oxygen is less than the percentage of oxygen in air.

The methods of the invention may involve culturing the pluripotent stem cells directly on the fiber scaffold. That is to say that the fiber scaffold has not been coated with, or otherwise treated with, one or more extracellular matrix (ECM) component, such as collagen, chitosan, fibrin, elastin, laminin, hyaluronan or gelatin. The method may not involve feeder cells, such as Mouse or Human Embryonic or Adult Fibroblast cells (mEF or hEF cells). For example, the fiber scaffold may not be coated with, or comprise a layer of, feeder cells.

Through the methods of the invention a population of pluripotent stem cells may be expanded (i.e. the number of cells is increased). Through the methods of the invention pluripotent stem cells may be cultured without loss of pluripotency (stemness). Through the methods of the invention progenitor cells within the culture of pluripotent stem cells do not lose pluripotency ("stemness"). In some cases the pluripotent stem cells are incubated for 10 days without loss of pluripotency.

In some methods the percentage of oxygen is in the range about 0.25% to about 20%, about 0.5% to about 10% or about 2%.

The method may be performed in vitro.

The methods of the invention may involve uncoated fibers. In this way pluripotent stem cells cultured in the methods of the invention are free from xenocontaminants, such as biological matrix materials or substrates, or feeder cells.

Fibers used in the methods of the invention may have a diameter of between 50 nm and 3000 nm or between 100 and 300 nm. The fibers may be randomly orientated or aligned. Preferably the fibres are aligned.

The fibers of the fiber scaffold are made from a synthetic polymer. In some cases the fibers comprise poly-ϵ-caprolactone (PCL).

In certain methods according to the invention, the pluripotent stem cells are human embryonic stem cells. The stem cells may be suitable for clinical use.

Some methods according to the invention involve the step of inducing the pluripotent stem cells to differentiate. Methods involving inducing the pluripotent stem cells to differentiate may involve adding differentiation media to the fibers seeded with pluripotent stem cells. In some cases pluripotent stem cells are detached from the fibers before adding differentiation medium.

The invention also encompasses pluripotent stem cells obtained by the methods disclosed herein. Such pluripotent stem cells may be useful in medicine.

The invention also provides an implant and a method for preparing an implant. The implant may be prepared by culturing pluripotent stem cells on a fiber scaffold. The fiber scaffold may be part of the implant, or the fiber scaffold may be connected to a pre-formed implant.

An implant according to the invention may comprise a fiber scaffold loaded with pluripotent stem cells, the pluripotent stem cells having been cultured on said fiber scaffold in a gas atmosphere in which the percentage of oxygen is less than the percentage of oxygen in air. The implant may be for use in medicine.

The invention also provides a method of treatment comprising culturing pluripotent stem cells on a fiber scaffold according in a gas atmosphere in which the percentage of oxygen is less than the percentage of oxygen in air, wherein the fiber scaffold is, or is connected to, an implant; and introducing the implant to a patient in need of treatment. The patient may be a human or non-human mammal.

DESCRIPTION OF PREFERRED EMBODIMENTS

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which.

Figures 1, 2:
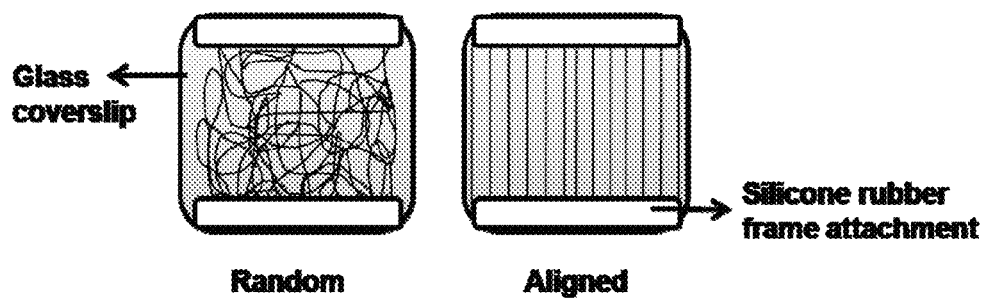
FIG. 1. Schematic diagram demonstrating the electrospun aligned and random nanofibers on glass coverslips with reinforced attachment using silicone rubber banding.
FIG. 2. Characterisation of electrospun nanofibrous substrates in both aligned and random conformations. (A) FESEM imaging of PCL (a and b), PLGA (c and d), PLLA (e and f) nanofibers, in both random and aligned conformations. Nanofiber diameters are presented under each image. An arrow indicates the predominant direction of aligned fibers. Scale bar=3 μm.

The invention provides methods for the culture of pluripotent stem cells. Through these methods cultures of stem cells are expanded, i.e. the number of cells is increased, as the stem cells undergo self-renewal. Through the methods of the invention pluripotency, or stemness, is maintained.

Stem Cells

The stem cells cultured and described herein may be pluripotent stem cells of any kind. Preferably they are embryonic stem cells (ESC) and more preferably they are human embryonic stem cells (hESC).

In this specification, by stem cell is meant any cell type that has the ability to divide for indefinite periods (i.e. self-renew) and give rise to specialized cells. An embryonic stem cell comprises a primitive (undifferentiated) cell from the embryo that has the potential to become a wide variety of specialized cell types. Stem cells are therefore cells which are not terminally differentiated and are able to produce cells of other types. The stem cells may be pluripotent or totipotent, but are preferably pluripotent.

Pluripotent Stem Cells

"Pluripotent stem cells" are true stem cells, with the potential to make any differentiated cell in the body.

Totipotent stem cells are a type of pluripotent stem cell with the potential to make any cell in the human body, including the extraembryonic membranes derived from the trophoblast.

Certain methods disclosed herein relate to the culture of pluripotent stem cells that are not totipotent, and do not contribute to making the extraembryonic membranes which are derived from the trophoblast. Several types of pluripotent stem cells have been found.

The term pluripotent stem cells as used herein includes totipotent stem cells, i.e. those cells that have the potential to become any cell type in the adult body, or any cell of the extraembryonic membranes (e.g. placenta). The only totipotent cells are the fertilized egg and the first 4 or so cells produced by its cleavage.

The number of pluripotent stem cells in a culture can be measured by measuring the number of colony forming units (CFUs).

Multipotent Stem Cells

Also referred to in this disclosure are multipotent stem cells. Multipotent stem cells are true stem cells but can only differentiate into a limited number of types, and are thus are distinct from pluripotent stem cells. For example, the bone marrow contains multipotent stem cells that give rise to all the cells of the blood but not to other types of cells. Multipotent stem cells are found in adult animals. It is thought that every organ in the body (brain, liver) contains them where they can replace dead or damaged cells.

Embryonic Stem Cells

Embryonic Stem (ES) cells may be isolated from the inner cell mass (ICM) of the blastocyst, which is the stage of embryonic development when implantation occurs.

Embryonic Germ Cells

Embryonic Germ (EG) cells may be isolated from the precursor to the gonads in aborted fetuses.

Embryonic Carcinoma Cells

Embryonic Carcinoma (EC) cells may be isolated from teratocarcinomas, a tumor that occasionally occurs in a gonad of a fetus. Unlike the first two, they are usually aneuploid. All three of these types of pluripotent stem cells can only be isolated from embryonic or fetal tissue and can be grown in culture. Methods are known in the art which prevent these pluripotent cells from differentiating.

Adult Stem Cells

Adult stem cells comprise a wide variety of types including neuronal, skin and the blood forming stem cells which are the active component in bone marrow transplantation. These latter stem cell types are also the principal feature of umbilical cord-derived stem cells. Adult stem cells can mature both in the laboratory and in the body into functional, more specialised cell types although the exact number of cell types is limited by the type of stem cell chosen.

Sources of Stem Cells

Stem cells cultured in the present invention may be obtained or derived from existing cultures or directly from any adult, embryonic or fetal tissue, including blood, bone marrow, skin, epithelia or umbilical cord (a tissue that is normally discarded).

Stem cells may be obtained from established cell lines, such as those maintained by ATCC.

In preferred arrangements of the present invention, stem cells generated and/or cultured comprise:

non-human stem cells e.g. rabbit, guinea pig, rat, mouse or other rodent (including stem cells from any animal in the order Rodentia), cat, dog, pig, sheep, goat, cattle, horse, non-human primate or other non-human vertebrate organism; and/or non-human mammalian stem cells and/or non-human embryonic stem cells, preferably non-human mammalian embryonic stem cells, more preferably mouse embryonic stem (mES) cells; and/or human stem cells, more preferably human embryonic stem cells (hES).

Embryonic Stem Cells

Embryonic stem cells may be isolated from blastocysts of members of primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998), Reubinoff et al, Nature Biotech. 18:399, 2000 and Ludwig et al Nat Biotech (2006) 24(2): 185-187.

Briefly, human blastocysts may be obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for embryonic stem cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 minutes (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh embryonic stem (ES) medium, and observed for colony formation. Colonies demonstrating undifferentiated morphology are individually selected by micropipette, mechanically dissociated into clumps, and replated. embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (.about.200 U/mL; Gibco) or by selection of individual colonies by micropipette. Clump sizes of about 50 to 100 cells are optimal.

Embryonic Germ Cells

Human Embryonic Germ (hEG) cells may be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 mm$^3$ chunks. The tissue is then pipetted through a 100/μL tip to further disaggregate the cells. It is incubated at 37 degrees C. for about 5 min, then about 3.5 mL EG growth medium is added. EG growth medium is DMEM, 4500 mg/L D-glucose, 2200 mg/L mM sodium bicarbonate; 15% embryonic stem (ES) qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant basic fibroblast growth factor (bFGF, Genzyme); and 10 μM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced and incubated 1 h or overnight at 37 degrees C., resuspended in 1-3 mL of EG growth medium, and plated onto a feeder layer.

Ninety-six well tissue culture plates are prepared with a sub-confluent layer of feeder cells cultured for 3 days in modified EG growth medium free of LIF, bFGF or forskolin, inactivated with 5000 rad y-irradiation. Suitable feeders are STO cells (ATCC Accession No. CRL 1503). 0.2 mL of primary germ cell (PGC) suspension is added to each of the wells. The first passage is conducted after 7-10 days in EG growth medium, transferring each well to one well of a 24-well culture dish previously prepared with irradiated STO mouse fibroblasts. The cells are cultured with daily replacement of medium until cell morphology consistent with EG cells are observed, typically after 7-30 days or 1-4 passages.

Induced Pluripotent Stem Cells

The methods and compositions described here may be used for the propagation of induced pluripotent stem cells. Induced pluripotent stem cells, commonly abbreviated as iPS cells or iPSCs, are a type of pluripotent stem cell artificially derived from a non-pluripotent cell, typically an adult somatic cell, by inserting certain genes. iPS cells are reviewed and discussed in Takahashi, K. & Yamanaka (2006), Yamanaka S, et. al. (2007), Wernig M, et. al. (2007), Maherali N, et. al. (2007) and Thomson J A, Yu J, et al. (2007) and Takahashi et al., (2007).

iPS cells are typically derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection.

Sources of Pluripotent Cells

Aspects and embodiments of the present invention are concerned with the use of pluripotent cells. Embryonic stem cells and induced pluripotent stem cells are described as examples of such cells.

Embryonic stem cells have traditionally been derived from the inner cell mass (ICM) of blastocyst stage embryos (Evans, M. J., and Kaufman, M. H. (1981). Establishment in culture of pluripotent cells from mouse embryos. Nature 292, 154-156. Martin, G. R. (1981). Isolation of a pluripotent cell line from early mouse embryos cultured in medium conditioned by teratocarcinoma stem cells. Proc. Natl. Acad. Sci. USA 78, 7634-7638. Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147). In isolating embryonic stem cells these methods may cause the destruction of the embryo.

Several methods have now been provided for the isolation of pluripotent stem cells that do not lead to the destruction of an embryo, e.g. by transforming adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell.

2. Reprogramming by fusion with embryonic stem cells. This technique involves the fusion of a somatic cell with an embryonic stem cell. This technique may also lead to the creation of animal-human hybrid cells, as in 1 above.

3. Spontaneous re-programming by culture. This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported (Jiang et al., Pluripotency of mesenchymal stem cells derived from adult marrow. Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu-Shinohara et al., Generation of pluripotent stem cells from neonatal mouse testis. Cell 119, 1001-1012, 2004).

4. Reprogramming by defined factors. For example the generation of iPS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication 1 Mar. 2009) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1-4 are described and discussed by Shinya Yamanaka in Strategies and New Developments in the Generation of Patient-Specific Pluripotent Stem Cells (Cell Stem Cell 1, July 2007 ᵃ2007 Elsevier Inc), incorporated herein by reference.

5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444:512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444:481-485. Chung Y, Klimanskaya I, Becker S, et al. Human embryonic stem cell lines generated without embryo destruction. Cell Stem Cell. 2008; 2:113-117 and Dusko Ilic et al (Derivation of human embryonic stem cell lines from biopsied blastomeres on human feeders with a minimal exposure to xenomaterials. Stem Cells And Development—paper in pre-publication), all incorporated herein by reference.

6. hESC lines obtained from arrested embryos which stopped cleavage and failed to develop to morula and blastocysts in vitro. See Zhang X, Stojkovic P, Przyborski S, et al. Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference.

7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2):152-61 who employed the chemical activation of nonfertilized metaphase II oocytes to produce stem cells.

8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by β-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et al (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599). Kim et al (Ex vivo characteristics of human amniotic membrane-derived stem cells. Cloning Stem Cells 2007 Winter; 9(4):581-94, incorporated herein by reference) succeeded in isolating human amniotic membrane-derived mesenchymal cells from human amniotic membranes. Umbilical cord is a tissue that is normally discarded and stem cells derived from this tissue have tended not to attract moral or ethical objection.

The present invention includes the use of stem cells obtained from any of these sources or created by any of these methods. In some embodiments, the stem cells used in the methods of the present invention have been obtained by a method that does not cause the destruction of an embryo. More preferably in some embodiments, the stem cells used in the methods of the present invention have been obtained by a method that does not cause the destruction of a human or mammalian embryo. As such, methods of the invention may be performed using cells that have not been prepared exclusively by a method which necessarily involves the destruction of human embryos from which those cells may be derived. This optional limitation is specifically intended to take account of Decision G0002/06 of 25 Nov. 2008 of the Enlarged Board of Appeal of the European Patent Office.

Pluripotency

Stem cells propagated by the methods of the invention retain pluripotency. All or a substantial portion of the propagated cells may retain pluripotency. This may be one of 50% or more, 60% or more, 70% or more, 80% or more, 90% or more, 93% or more, 95% or more, 97% or more, 98% or more, 99% or more, or substantially 100% of the propagated stem cells. This may be measured as the number of colony forming units that are retained in the propagated cells. Preferably, at least 20%, or at least 30%, or at least 40%, or at least 50%, or at least 60%, or at least 70%, or at least 80%, or at least 90%, or at least 95% or 100% of the propagated cells in the culture are colony forming units.

"Stemness" as used herein refers to pluripotency. Through the methods of the invention, pluripotent stem cells may be cultured without loss of pluripotency (stemness) for more than 10 days, more than 15 days, more than 20 days, more than 25 days, more than 30 days, more than 35 days or more than 40 days. In some cases stemness is maintained for at least 21 days.

Cultures of pluripotent stem cells (pPS) obtained using the methods of the invention are preferably substantially free of differentiated cells. "Substantially free of differentiated cells" includes populations of pluripotent stem cells with less than 5%, less than 3% or less than 1% differentiated cells.

Pluripotency may be assessed in one or more of the following ways:
  Determining the capacity of the cells to differentiate into all three cellular lineages, i.e., endoderm, ectoderm and mesoderm. Methods of induction of stem cells to differentiate each of these lineages are known in the art and may be used to assay the capability of the propagated stem cells; and/or
  Determining the expression of one or more markers of pluripotency; and/or
  Examining morphology of the cells As such, the stem cells propagated by the methods disclosed herein may display any of the following stem cell characteristics.

Stem cells may display increased expression of Oct4 and/or SSEA-1. Expression of any one or more of Flk-1, Tie-2 and c-kit may be decreased. Stem cells which are self-renewing may display a shortened cell cycle compared to stem cells which are not self-renewing.

Stem cells may display defined morphology. For example, in the two dimensions of a standard microscopic image, human embryonic stem cells display high nuclear/cytoplasmic ratios in the plane of the image, prominent nucleoli, and compact colony formation with poorly discernable cell junctions.

Stem cells may also be characterized by expressed cell markers as described in further detail below.

Expression of Pluripotency Markers

The pluripotency of the generated stem cells may be determined by use of suitable assays. Such assays may comprise detecting one or more markers of pluripotency, e.g. SSEA-1 antigen, alkaline phosphatase activity, detection of Oct-4 gene and/or protein expression, by observing the extent of teratoma formation in SCID mice or formation of embryoid bodies.

The pluripotency of hESC may be defined by the expression of markers such as Oct-4, SSEA-4, Tra-1-60, Tra-1-81, SOX-2, GCTM-2, FOXD3, PODXL, alkaline phosphatase, OCT-4, SSEA-4 and TRA-1-60. Any one or more of these pluripotency markers may be retained by the propagated stem cells.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Lines from Human Germ Cell Tumors, in E. J. Robertson, 1987, supra). Human embryonic stem cells are typically SSEA-1 negative and SSEA-4 positive. hEG cells are typically SSEA-1 positive. Differentiation of pPS cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Detection of markers may be achieved through any means known in the art, for example immunologically. Histochemical staining, flow cytometry (FACS), Western Blot, enzyme-linked immunoassay (ELISA), etc may be used.

Flow immunocytochemistry may be used to detect cell-surface markers. Immunohistochemistry (for example, of fixed cells or tissue sections) may be used for intracellular or cell-surface markers. Western blot analysis may be conducted on cellular extracts. Enzyme-linked immunoassay may be used for cellular extracts or products secreted into the medium. For this purpose, antibodies to the pluripotency markers as available from commercial sources may be used.

Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M. et. al. (2000). J. Cell Science 113: 5-10.).

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez). See U.S. Pat. No. 5,843,780 for further details.

Substantially all of the propagated cells, or a substantial portion of them, are pluripotent and/or express the marker(s). For example, the percentage of cells in the culture that are pluripotent and/or express the marker or markers may be 50% or more, 60% or more, 70% or more, 80% or more, 90% or more, 93% or more, 95% or more, 97% or more, 98% or more, 99% or more, or substantially 100%.

Cell Viability

Using the methods of the invention, the pluripotent stem cells may retain cell viability for the number of days, or number of passages described herein. Cell viability may be assayed in various ways, for example by Trypan Blue exclusion.

A protocol for vital staining follows. Place a suitable volume of a cell suspension (20-200 µL) in appropriate tube add an equal volume of 0.4% Trypan blue and gently mix, let stand for 5 minutes at room temperature. Place 10 µl of stained cells in a hemocytometer and count the number of viable (unstained) and dead (stained) cells. Calculate the average number of unstained cells in each quadrant, and multiply by $2 \times 10^4$ to find cells/ml. The percentage of viable cells is the number of viable cells divided by the number of dead and viable cells.

The viability of cells in the culture may be 50% or more, 60% or more, 70% or more, 80% or more, 90% or more, 93% or more, 95% or more, 97% or more, 98% or more, 99% or more, or substantially 100%.

Stem Cells Obtained Using the Methods of the Invention

The present invention provides cultures of pluripotent stem cells with high numbers of cells. Through the methods of the invention the pluripotency of the culture of cells is maintained such that progenitor cells in the culture maintain the ability to differentiate into all three cellular lineages.

The stem cells generated by any of the methods of the present invention may be used in a method of medical treatment. The method of medical treatment may comprise administering to an individual in need of treatment a therapeutically effective amount of stem cells obtained by the culture method described herein. The stem cells may be formulated as a medicament or pharmaceutical composition.

Stem cells obtained through culture methods and techniques according to this invention may be used to differentiate into another cell type for use in a method of medical treatment. Thus, the differentiated cell type may be derived from, and may be considered as a product of, a stem cell obtained by the culture methods and techniques described which has subsequently been permitted to differentiate.

Pharmaceutical compositions and medicaments may be provided comprising stem cells generated by any of the methods of the present invention, cells differentiated from such pluripotent stem cells, or fragments or products thereof. The pharmaceutical compositions optionally further include a pharmaceutically acceptable carrier, adjuvant or diluent. Such pharmaceutical composition may be useful in a method of medical treatment.

Differentiation/Embryoid Bodies

Stem cells cultured using the methods of the invention may be differentiated into any suitable cell type.

Methods of differentiating stem cells are known in the art and are described in for example ltskovitz-Eldor (2000) and Graichen et al (2007). The cultured stem cells may also be used for the formation of embryoid bodies. Embryoid bodies, and methods for making them, are known in the art. The term "embryoid body" refers to spheroid colonies seen in culture produced by the growth of embryonic stem cells in suspension. Embryoid bodies are of mixed cell types, and the distribution and timing of the appearance of specific cell types corresponds to that observed within the embryo. Embryoid bodies may be generated by plating out embryonic stem cells onto media such as semi-solid media. Methylcellulose media may be used as described in Lim et al, Blood. 1997; 90:1291-1299.

Embryonic stem cells may be induced to form embryoid bodies, for example using the methods described in ltskovitz-Eldor (2000). The embryoid bodies contain cells of all three embryonic germ layers.

The embryoid bodies may be further induced to differentiate into different lineages for example by exposure to the appropriate induction factor or an environmental change. Graichen et al (2007) describes the formation of cardiomyocytes from human embryonic stem cells by manipulation of the p38MAP kinase pathway. Graichen demonstrates induction of cardiomyocyte formation from stem cells by exposure to a specific inhibitor of p38 MAP kinase such as SB203580 at less than 10 µm.

Differentiated cells may be employed for any suitable purpose, such as regenerative therapy, as known in the art.

Fibers/Scaffolds

Fibers useful in the methods of the invention are made from synthetic or natural polymers. The fibers may be nanofibers. Suitable synthetic polymers include polyesters, polyurethane polymers and polyethersulfone polymers, for example poly-ε-caprolactone (PCL), poly lactic-co-glycolic acid and poly-L-lactic acid. The fibers may comprise an aliphatic polyester. The fibers may be hydrophobic. In particular, the fibers may comprise poly-ε-caprolactone, poly L,D lactic-glycolic acid (PLGA), poly L,D lactic acid or poly vinyl alcohol. The fibers may consist or comprise polymethylgultarimide (PMGI). Preferably the fibers consist of, or comprise poly-ε-caprolactone. The natural polymers include poly(HydroxyAlkanoate), silk fibroin and cellulose.

The fibers may be produced by electrospinning. Methods of electrospinning are known. In a sample method of electrospinning, electrospinning solutions may be prepared by dissolving a polymer in chloroform and dimethylformamide. The dissolved polymer is fed into a syringe attached to a needle using a syringe pump. A voltage is applied using a high-voltage power supply, to draw the polymer from the needle, onto a collector.

Random fiber scaffolds may be fabricated by deposition to a static, negatively charged collector [31, 27]. Various methods for collecting aligned fiber scaffolds are known, including using a rotating mandrel [27] or a steel frame with an air gap [29]. In an aligned fiber scaffold the longitudinal axes of individual fibers run substantially in parallel. It is not necessary that the axes are precisely parallel, but that the majority of fibers are orientated in substantially the same direction.

In the methods of the invention the fibers are preferably aligned.

The fiber scaffold may be attached to a glass coverslip. In this case fiber scaffold attachment may be further reinforced with silicone rubber strips (Silex Ltd, Borden, UK), adhered using silicone glue (RS Scientific, Corby, UK) as shown in FIG. 1. Scaffolds may be allowed to dry before sterilisation and cell seeding.

Fibers useful in the methods of the invention preferably have a diameter of less than 3000 nm. The fibres may have a diameter of less than 2900 nm, less than 2800 nm, less than 2700 nm, less than 2600 nm, less than 2500 nm, less than 2400 nm, less than 2300 nm, less than 2200 nm, less than 2100 nm, less than 2000 nm, less than 1900 nm, less than 1800 nm, less than 1700 nm, less than 1600 nm, less than 1500 nm, less than 1400 nm, less than 1300 nm, less than 1200 nm, less than 1100 nm, less than 1000 nm, less than 900 nm, less than 800 nm, less than 700 nm, less than 600 nm, less than 500 nm, less than 400 nm, less than 300 nm, less than 200 nm, less than 100 nm, less than 90 nm, less than 80 nm, less than 70 nm, less than 60 nm, less than 50 nm, less than 40 nm or less than 30 nm. The fibers used in the method of the invention preferably have a diameter of less than 350 nm. Fibers having a diameter of less than 1200 nm are considered to be 'nanofibers'. Preferably, the fibers of the invention are nanofibers. This value may be the average diameter of fibers in the scaffold. The average diameter of the fibers may be calculated as the mean of a sample of fibers, for example the mean of 20 fibers.

Preferably the fibres have a diameter of more than 50 nm, more than 60 nm, more than 70 nm, more than 80 nm, more than 90 nm, more than 100 nm, more than 110 nm, more than 120 nm, more than 130 nm, more than 140 nm, more than 150 nm, more than 160 nm, more than 170 nm, more than 180 nm, more than 190 nm, more than 200 nm, more than 210 nm, more than 220 nm, more than 230 nm, more than 240 nm, more than 250 nm, more than 260 nm, more than 270 nm, more than 280 nm or more than 290 nm. Preferably there are substantially no fibers with a diameter of more than 350 nm, preferably not more than 320 nm, preferably not more than 300 nm.

The fibres may have a diameter in the range of between about 20 nm and about 120 nm, between about 200 nm and about 1000 nm, between about 200 nm and about 500 nm, between about 200 nm and about 400 nm or between about 200 and about 300 nm.

Fiber diameter may be controlled in a number of ways. For example, through the choice of polymer (e.g. PCL vs PLA), use of different solvents (for example using PCL dissolved in chloroform and DMF or in acetic acid or in acetone), use of different concentrations of polymer (e.g. 14% vs 10%), different voltage (e.g. ±4 kV vs ±7 kV), different needle size (e.g. 18 G vs 22 G) or different working distance between the electrodes (e.g. 10 cm vs 20 cm). A person skilled in the art of polymer electrospinning[51, 52] will be readily able to produce fibers of a chosen diameter using one or more of these approaches to modifying fiber size.

The fibers of the invention may be spun from 15% or lower concentration of PCL. In some cases, the fiber is spun from 12.5% PCL. For example, between 6 and 20%, between 7 and 15%, between 7.5 and 12.5% or between 9 and 12% polymer solution. The fibers may be spun from 15%, 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, or lower concentration of polymer. The polymer may be PCL.

Two or more different polymers may be co-spun in order to mix different fibers, each composed of a different material or materials. Alternatively, a mixture containing two or more polymers may be spun to give a scaffold comprising fibers of a mixed composition.

By manipulating the composition of the scaffold, either by producing fibers containing a mixture of two or more polymers, or by mixing multiple fibers of different polymers, the diameter of the fibers may be altered. Similarly, mixing multiple polymers will enable other properties of the fibers and the scaffold, For example, different polymers exhibit different protein adsorption characteristics so, by using a combination of two or more polymers, either within the same fiber, or by mixing a plurality of different types of fiber, the adsorption properties of the scaffold may be manipulated. Similarly, by manipulating the polymers used to make up the scaffold, the physical properties of that scaffold may be regulated, for example the flexibility, longevity or thermal stability of the scaffold may be regulated.

Fibers may be hydrophobic or hydrophilic. Preferably, the fibers are hydrophobic.

Preferably the fibers and/or fiber scaffold useful in the methods of the invention are uncoated. The terms "naked" or "uncoated" as used herein refer to fibers which have not been coated with a biological substrate or biological matrix, or with mitotically inactivated feeder cells. For example, the fibers may not have been coated with, or otherwise treated with, one or more components of the extracellular matrix (ECM), including collagen, chitosan, fibrin, elastin, laminin, hyaluronan or gelatin. In some cases, the fibers and/or fiber scaffold has not had a layer of biological substrate, biological matrix, or feeder cells applied to it. Thus, the methods of the invention involve the culture of cells directly on the fibers and/or fiber scaffold.

The methods of the invention preferably do not involve the use of feeder cells, such as mitotically inactivated fibroblast cells. Preferably, in the methods of the invention the fibers are not coated with a biological substrate or biological matrix, such as Matrigel™, collagen or gelatine.

Preferably, methods of expanding pluripotent stem cells according to the invention are not performed in the presence of differentiation medium.

Following the culture methods of the invention the pluripotent stem cells may be induced to differentiate, and thus differentiation medium may be added to the culture of pluripotent stem cells. Alternatively, following culture according to the methods of the invention the pluripotent stem cells may be detached from the fiber scaffold and then induced to differentiate.

As discussed above, methods of differentiation are well known. For example stem cells may be induced to differentiate into adipocytes through the addition of differentiation medium containing Dulbecco's modified Eagle's medium (DMEM) supplemented with L-glutamine, fetal bovine serum (FBS), dexamethoason, insulin, indomethacin and isobutylmetylxanthine [27].

The stem cells may be detached from the fiber scaffold by methods known in the art. In one exemplary method, the cells on the scaffold are washed with PBS and then a 0.25% Trypsin/EDTA treatment followed by the addition of a 5-fold excess volume of fresh media, before transfer into a centrifuge tube and centrifugation at 1000 rpm for 2-5 minutes. Media is then removed from the tube taking care not to disturb the cell pellet. The cells in the cell pellet may then be used for reseeding, transplant, differentiation, or for other uses of stem cells known in the art.

Implants

Fiber scaffolds seeded with pluripotent stem cells may be useful in both medical and veterinary purposes. It will be appreciated that the present invention may improve the quality of life of a patient or potentially extend the life of an animal, for example a valuable race horse for use in breeding.

In particular, fiber scaffolds seeded with pluripotent stem cells may be useful in an implant or prosthesis. Such an implant or prosthesis would be useful for tissue engineering. The implant or prosthesis should be biocompatible, i.e. non-toxic and of low immunogenicity (most preferably non-immunogenic). The implant may be biodegradable such that the implant degrades as wound healing occurs, ultimately leaving only the regenerated tissue in situ in the subject. Alternatively a non-biodegradable implant may be used, e.g. to guide bone regeneration over a large discontinuity, with surgical removal of the implant optionally being a requirement after successful wound healing.

Oxygen

The methods of the present invention involve culture of cells in a surrounding gas atmosphere in which the percentage of oxygen is controlled, the gas atmosphere being in contact with the cultured cells. The percentage of oxygen is controlled so as to be lower than the percentage of oxygen in an external atmosphere, where the external atmosphere is typically the gas atmosphere immediately external to the culture environment, e.g. outside the incubator apparatus in which the cells are being cultured. The external atmosphere will therefore commonly be air at room temperature and pressure. As such, by "external atmospheric $O_2$ concentration" or "percentage of oxygen in air", is meant the normal or ambient atmospheric $O_2$ concentration that is found outside the controlled atmosphere of the culture. Typically, this $O_2$ concentration is about 21%.

In the methods of the invention the fiber scaffold is incubated in $O_2$ with a concentration that is less than the normal atmospheric concentration (typically about 21%). The oxygen concentration may be less than 20.5%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, less than 1%, less than 0.5% or less than 0.25%. Preferably, the concentration of $O_2$ is more than one of about 0.25%, about 0.5%, or about 1%. The oxygen concentration may be in the range of between about 0.25% and about 5%, between about 1% and about 5%, between about 2% and about 5%, between about 1% and about 4%, between about 1% and about 3%. In a highly preferred embodiment, the concentration of $O_2$ is maintained at about 2%.

In the method of the invention, fiber scaffolds seeded with pluripotent stem cells are not incubated in ambient atmospheric $O_2$ concentrations (normoxia), or in hyperoxic conditions, such as 21% or more $O_2$. Instead, the methods of the invention involve an $O_2$ concentration which is less than that of ambient atmospheric $O_2$, i.e. hypoxia.

Oxygen levels may be controlled by methods known in the art including, for example culturing fibers seeded with pluripotent stem cells in a controlled environment incubator (WO2009/007692).

The invention provides methods for the culture of pluripotent stem cells which have uses in research, therapy and regenerative medicine.

DETAILED DESCRIPTION OF THE INVENTION

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

EXAMPLES

Example 1

Materials and Methods

Fabrication of Nanofiber Scaffolds Via Electrospinning

PCL, PLGA and PLLA were electrospun in two different conformations (aligned or random) onto glass coverslips (24×24 mm). Electrospinning solutions were prepared by dissolving each polymer in chloroform and dimethylformamide; Table 1. Random nanofiber scaffolds were fabricated by deposition to a static, negatively charged collector. The aligned nanofiber scaffolds were collected using a rotating mandrel (ca. 5,250 rpm), as described previously by our group [27]. The types of the nanofiber scaffolds were denoted via suffixing R for random and A, for aligned after the polymer name. Example of electrospinning parameters used to attain each type of scaffold are stated in Table 1. PCL was also electrospun at two different concentrations (12.5% and 15%) in both aligned and random conformations in order to attain PCL nanofibrous substrates with various fiber diameters. Nanofiber scaffold attachment on glass coverslips was further reinforced with silicone rubber strips (Silex Ltd, Borden, UK), adhered using silicone glue (RS Scientific, Corby, UK) as shown in FIG. 1. Scaffolds were allowed to dry for 3-4 hours before sterilisation and cell seeding.

TABLE 1

Example of polymer and electrospinning operating parameters used to fabricate aligned and random nanofibrous scaffolds

| Parameter | 12.5% PCL | 7% PLLA | 2% PLGA |
| --- | --- | --- | --- |
| Flow Rate (ml/min) | 0.01 | 0.025 | 0.01 |
| Needle | 22 G blunt needle | 18 G blunt needle | 22 G blunt needle |
| Working Distance (cm) | Aligned = 20<br>Random = 15 | Aligned = 20<br>Random = 15 | Aligned = 20<br>Random = 15 |
| Voltage (kV) | Aligned = 4.5<br>Random = 4 | Aligned = 7<br>Random = 6 | Aligned = 3.5<br>Random = 4 |
| Solvent & Ratio | CHL/DMF (7:3) | CHL/DMF (9:1) | CHL/DMF (7:3) |

Sterilisation of Scaffolds

All nanofiber scaffolds and controls were sterilised by immersion in 70% industrial methylated spirit (IMS) for at least one hour. After this, IMS was aspirated off and the scaffolds were air-dried in non-adherent petri dishes (Sterilin, Newport, UK).

Expansion of Human Embryonic Stem Cells hESCs (SHEF1) were cultured on Matrigel™ (BD Biosciences, Oxford, UK) and conditioned culture media was prepared using mouse embryonic fibroblasts (MEFs) as described previously [32]. hESC media was composed of Knock-out DMEM (Gibco-Invitrogen, Paisley, UK) supplemented with 20% Knock-out Serum Replacement (Gibco-Invitrogen, UK), 1% L-glutamine (Lonza, Slough, UK), 1% non-essential amino acids (Lonza, Slough, UK), 4 ng/ml basic fibroblastic growth factor (Lonza, Slough, UK) and 0.1 mM β-mercaptoethanol (Gibco-Invitrogen, UK). hESC media was conditioned overnight on sub-confluent MEFs and then further supplemented with 4 ng/ml of bFGF and sterile filtered (Millipore, Watford, UK) before use.

hESCs were cultured and expanded in two different oxygen tensions; 2% $O_2$ (using a modular modification of a Galaxy $R^+$ incubator; RS Biotech, Irvine, UK) and 21% $O_2$ (Heraeus Cytoperm 2 incubator; Thermo Electron Corporation, UK). Media was changed daily and cells passaged every 2-3 days after reaching 90% confluence using a brief 0.25% Trypsin/EDTA treatment.

Seeding of hESCs onto Nanofiber Scaffolds

Nanofibrous scaffolds and controls (Matrigel-coated coverslips) were seeded with hESCs (SHEF 1, Passage 42), cultured and expanded in either 2% or 21% $O_2$ conditions. Cell seeding density was 1700 cells/$cm^2$ per scaffold or per Matrigel™ (control) sample; this was determined to be the optimum by previous experiments (data not shown). hESC were seeded in 500 μl of media which was pipetted directly onto the nanofiber scaffold or Matrigel™ coated (control) coverslip. All samples were incubated in their relevant oxygen levels (2% or 21% $O_2$) overnight, after which, each petri dish was flooded with 6 ml of MEF-conditioned hESC media and colonies were recovered over a 21 day period without change of media. For each sample type (Matrigel™ and scaffolds), at each oxygen tension, n=3.

Characterisation of Pluripotency of hESCs hESCs formed colonies expanded on Matrigel™ and PCL nanofibrous substrates (Aligned and Random) were cultured in physiological normoxia (2% $O_2$) for 21 days before immunostaining for pluripotent markers. Media was removed and hESC colonies were fixed in 4% paraformaldehyde (in PBS) for 40 min, washed with PBS, treated with 0.5% Triton-X for 5 min and non-specific proteins were blocked with 3% bovine serum albumin for 1 hour at room temperature. hESC colonies were then incubated with 1 μg/100 μL working solution of primary anti-human monoclonal antibodies; mouse anti-alkaline phosphatase, goat anti-Nanog and goat anti-Oct-3/4 overnight at 2-8° C. hESCs were washed three times with PBS; antibody alkaline phosphatase was treated using secondary antibody donkey anti-mouse IgG (NL557; R & D Biosystems) and antibodies Nanog and Oct-3/4 were treated using secondary antibody donkey anti-goat IgG (NL003; R & D Biosystems) at 5 μg/mL for two hours at room temperature. Nuclei were visualised by staining with DAPI and mounted using Vectashield (Vector Laboratories, Burlingame, Calif.). Images were recorded on a fluorescent microscope (Nikon TZ1; Leica, Germany).

Spontaneous Differentiation of hESCs

After 21 days culture, hESC colonies on PCL nanofiber scaffolds were placed in spontaneous differentiation media consisting of Knock Out-DMEM, 10% foetal bovine serum, 1% L-glutamine, 1% Non-essential amino acids and 0.1 mM β-mercaptoethanol. Culture of hESC colonies was continued for a further 21 days in 2% $O_2$ only. Cell lysis was performed in situ at specific time points ranging from day 0 to day 20 for subsequent RNA extraction. Cell lysates were prepared and homogenised as per manufacturer's protocol (RNeasy, Qiagen, Crawley, UK) and stored at −80° C. ready for subsequent RNA extraction.

Semi-Quantitative RT-PCR Analysis

RNA was extracted using the RNeasy Mini Kit according to manufacturer's instructions (Qiagen, Crawley, UK) and quantified on a Nanodrop spectrophotometer (ND1000; Thermo Scientific, Dorset, UK). Semi-quantitative RT-PCR (reverse transcriptase polymerase chain reaction) analysis was performed on RNA samples for hESCs cultured on all scaffold types (positive control, PCL aligned and random) at all time points (0, 5, 10 and 20 days). One-step RT-PCR was performed using the SuperScript® III One-Step RT-PCR System with Platinum® Taq DNA Polymerase (Invitrogen, Paisley, UK) according to manufacturers instructions. Primers (F indicates Forward Primer, R indicates Reverse Primer, annealing temperature used is indicated for each primer pair) were designed for GAPDH (F, 5'TGAAGGTCGGAGT-CAACGGATTTGGT'3, R, 5'CATGTGGGCCATGAGGTC-CAC CAC'3 56° C.), POU5F1 (F, 5'GCAATTTGC-CAAGCTCCTGAAGCAG'3, R, 5'CATAGC CTGGGGTACCAAAATGGGG'3, 56° C.), hTERT (F, 5'GCAGCTCCCATTTCATCAGC'3, R, 5'CAGGATG-GTCTTGAAGTCTG'3, 58° C.), SOX1 (F, 5'CCAG-GAGAACCCCAAGA GGC'3, R, 5'CGGCCAGCGAG-TACTTGTCC'3, 56° C.), ACTC-1 (F, 5'CATCCTGACCCT GAAGTATCCCATC'3, R, 5'CCCTCATAGATGGGGA-CATTGT GAG'3, 56° C.) and AFP (F, 5'CAGAAAAATG-GCAGCCACAGC'3, R, 5'TGGCAGCATTTCTCCAA-CAGG'3, 54° C.) using Primer3 freeware [33]. All RT-PCR reactions consisted of 50° C. for 30 minutes, 94° C. for 2 minutes, 30 cycles: 94° C. for 15 seconds, primer specific annealing temperature (see above) for 30 seconds, and 68° C. for 1 minute followed by a final extension of 68° C. for 5 minutes. Gel electrophoresis was performed to confirm PCR product amplification.

Colony Quantification

After 21 days of culture, hESCs on scaffolds or controls were washed twice with PBS, fixed in 95% methanol for 10 minutes, and immersed in 100% Giemsa stain (Sigma-Aldrich, Gillingham, UK) for 30 minutes. All samples were washed thoroughly with water to remove background staining. Samples were subsequently air-dried and colonies were visually recorded.

Microscopy Analysis

Light microscopy was performed using a bright field Nikon Eclipse TS-100 light microscope equipped with a Canon EOS 400D digital SLR camera. Representative images were taken of various samples at x10, x20 and x40 magnifications in different areas of the samples.

Field Emission Scanning Electron Microscopy (FESEM) samples were coated with gold using an Emscope 200 (Emscope, UK) sputter coater for two minutes prior to analysis. Samples were analysed using a Hitachi F4500, (Hitachi, UK) FESEM. FESEM images of nanofibers were analysed using Image J. Image J was calibrated according to the image magnification and the diameters of individual fibers were measured. Two separate nanofiber sub-samples were examined in a minimum of three different areas. Once the data for the measurements was collected for each polymer/orientation, the average nanofiber diameter and standard deviations were calculated.

Statistical Analysis

Error bars on graphs indicate standard deviations (SD). Data were tested for normality and a 1-way ANOVA/Kruskall Wallis test was performed followed by an appropriate posttest (Tukey's or Dunns, respectively) to determine the origins of significance. In this study significance levels are indicated according to the legend $p<0.05^*$, $p<0.01^{}$ and $p<0.001^{*}$.

Example 2

Characterisation of Nanofibers

Figure 3:
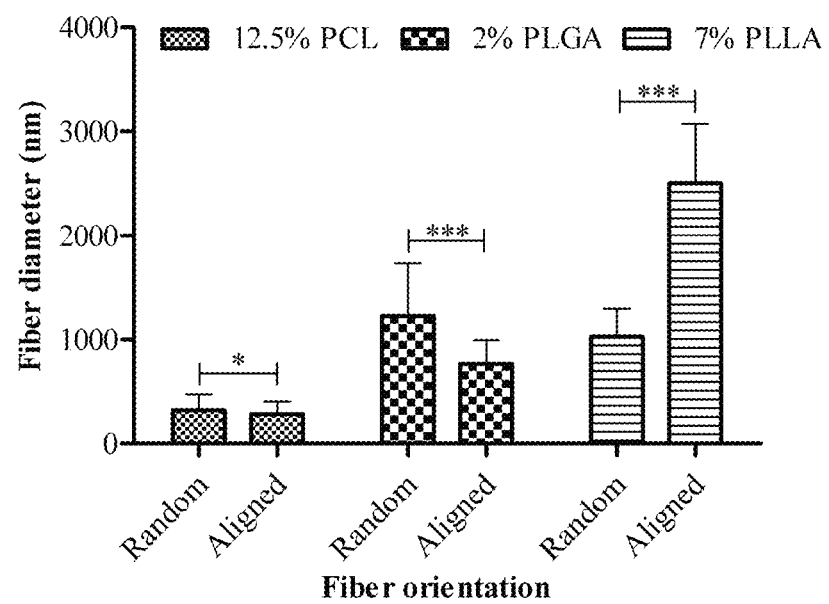
FIG. 3. Average diameters for PCL, PLGA, and PLLA nanofibers electrospun in both random and aligned conformations. Values indicate mean fiber diameter and standard deviation of n=20; *p<0.05, p<0.01, *p<0.001.

Random and aligned nanofibers of three different polymers were electrospun. Alignment was achieved using a mandrel rotating and via manipulation of the electrospinning parameters, including voltage and working distance. Random nanofibers were acquired by electrospinning directly onto coverslips attached to a static, negatively charged collector. Electrospun nanofibers were characterised by FESEM to visualise the morphology and diameter of both random and aligned fibers and to give an indication of surface topography (FIG. 2). PCL nanofibers had a smaller diameter in comparison to PLLA and PLGA nanofibers, in both aligned and random conformations. Significant differences in the fiber diameters between aligned and random conformations were apparent within each polymer type when electrospun with the same concentration of the solution (FIG. 3). PLLA-A fibers had a significantly greater fiber diameter in comparison to PLLA-R fibers whereas; PLGA-R fibers had a significantly greater diameter than aligned counterparts.

Determination of Colony Forming Units on Nanofibrous Surfaces

Figure 4A:
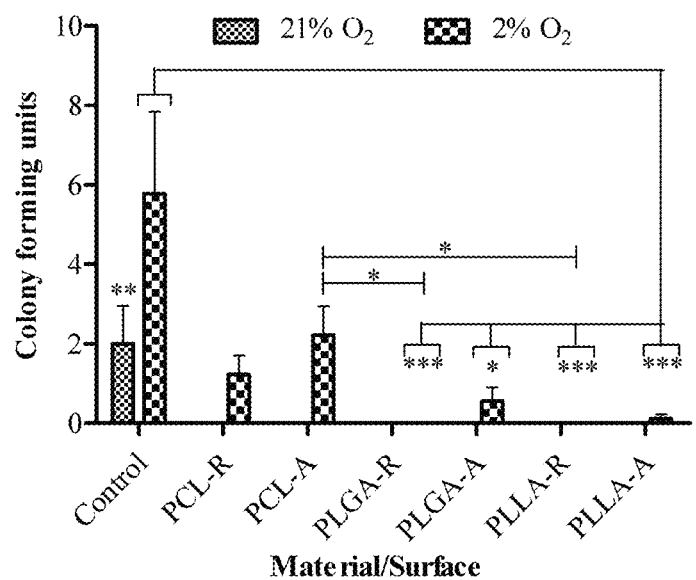
FIG. 4. (A) Quantification of colony forming units on control and nanofibrous surfaces under physiological normoxia (2%); (B) Embryoid body like clusters formed on nanofibrous surfaces in hyperoxia (21%). Values indicate mean number of forming units and standard deviation of n=9; *p<0.05, p<0.01, *p<0.001
Figure 4B:
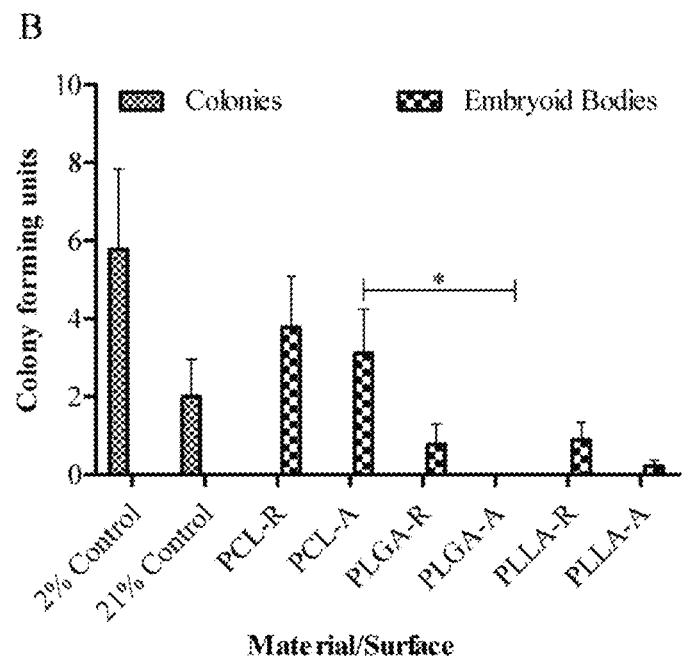

As anticipated, the Matrigel-coated glass coverslip yielded significantly more hESC colonies than any other surface in both 2% $O_2$ and 21% $O_2$ conditions (FIG. 4). PCL nanofibers proved to be the most efficient polymer for the adherence and expansion of hESCs, particularly PCL-A. However, it was strongly evident that the attachment of hESCs and their subsequent expansion into colonies was possible in 2% $O_2$ only. hESC morphology within the colonies (FIG. 5) and the colony appearance and size (FIG. 6a-b) were similar between the positive control and the nanofibrous substrates in 2% $O_2$. The frequency of colony formation was broadly similar for PLGA and PLLA irrespective of fiber orientation. However PCL-A provided a 2-fold increase over PCL-R. The overall schema of colony formation and expansion in 2% $O_2$ is as follows: Matrigel™ >PCL-A>PCL-R>PLGA-A>PLLA-A>PLGA-R=PLLA-R. This indicates that isolation and expansion of hESCs could be performed on all aligned nanofibrous surfaces and that irrespective of polymer, aligned electrospun fibers were preferable to random fibers. Larger colonies were observed on PCL-A in comparison to PCL-R and all other aligned substrates. However, PCL appeared to be the overall preferential polymer type in comparison to PLLA and PLGA for hESC colony formation and expansion.

In 21% $O_2$, recovery of hESC colonies on nanofibrous substrates was not apparent. However, we did note the attachment of tight, darkly stained, clusters of cells which had a morphological appearance similar to the mature EBs formed on gelatin-coated substrates (FIG. 6c-d). The greatest number of these EB-like (EBL) cell clusters was seen on PCL nanofibers in comparison to all other polymer types. In particular, PCL-A supported the greatest number of EBL clusters. EBL clusters were not observed on Matrigel-coated coverslips in 21% $O_2$. Overall schema for EBL clusters formation in 21% $O_2$ is as follows: PCL-A>PCL-R>PLGA-R>PLGA-A, PLLA-R and PLLA-A (FIG. 4).

Characterisation of Colonies Versus Embryoid Bodies on Nanofibrous Substrates

Figure 5:
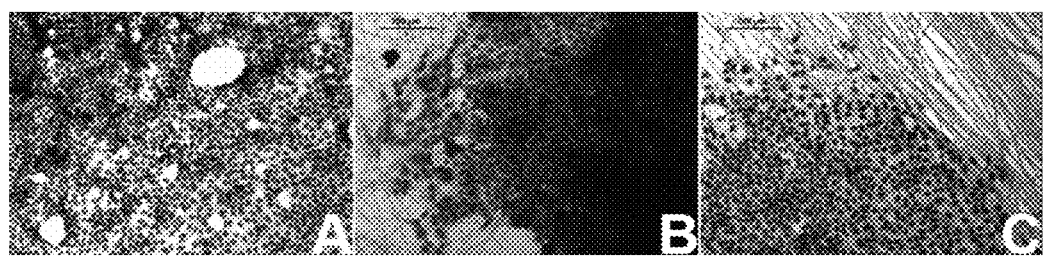
FIG. 5. Characterisation of hESC and colony morphology; hESC morphology within a colony, formed on (under physiological normoxia): (A) Matrigel™ (Positive control), (B) PCL random nanofibers and (C) PCL aligned nanofibers, Scale bar=200 μm.
Figure 6:
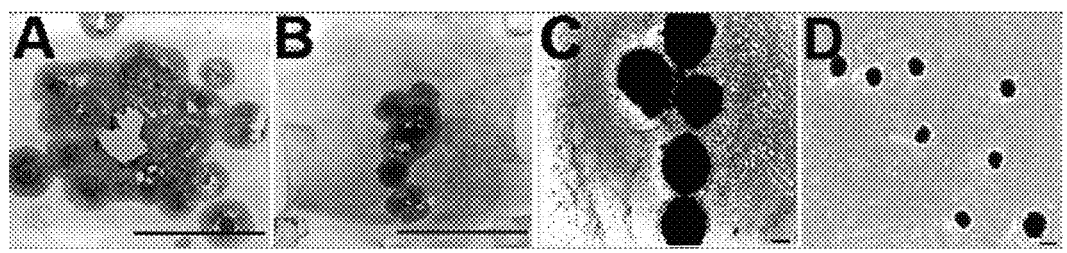
FIG. 6. Colony formation on: (A) Positive control (Matrigel™) and (B) PCL aligned nanofibrous scaffold under physiological normoxia; in comparison to Embryoid body-like clusters being formed under hyperoxia on PCL aligned (C) and (D) Gelatine-coated control (Scale bar=12 mm for A-B and 200 μm for C-D)
Figure 7:
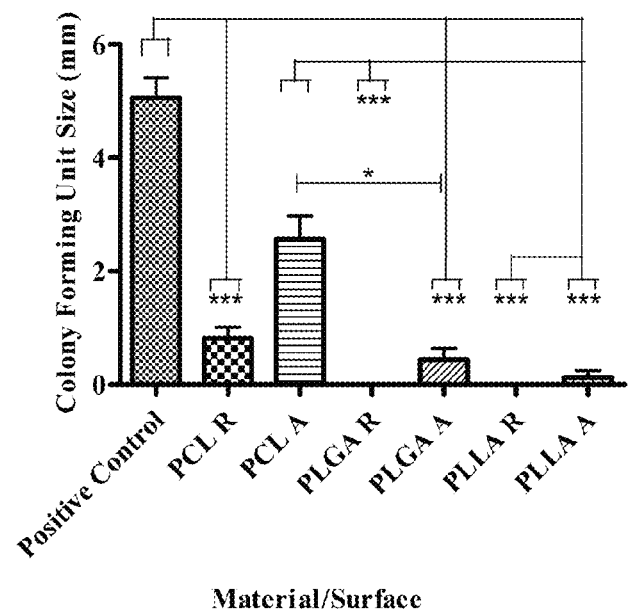
FIG. 7. Quantification of colony size of ES colonies formed on positive control and nanofibrous surfaces in physiological normoxia. Values indicate mean colony size and standard deviation of n=9; *p<0.05, p<0.01, *p<0.001.

The morphology of hESC colonies expanded on nanofibrous substrates in physiological normoxia was broadly similar to those cultured on Matrigel™ coated surfaces (FIGS. 5 and 6). hESC colonies recovered on random nanofibers appeared to be more dense and compact when compared to their aligned counterparts (FIG. 5b-c). The size of hESC colonies was determined by manually measuring the diameter of each colony formed on all scaffold types in 2% $O_2$. The positive control supported the recovery of significantly larger colony sizes than any of the nanofibrous surfaces. However, amongst the nanofibrous substrates, PCL-A supported significantly larger colony sizes when compared to all other polymers tested (FIG. 7).

On the contrary, hESCs cultured and expanded in hyperoxia on nanofibrous substrates, regardless of polymer type and fiber orientation, appeared to have an EB-like morphology and completely differed in structure when compared to colonies formed in physiological normoxia. These were characterised as dense, compact structures with a similar morphology to embryoid bodies formed on gelatine-coated tissue culture plastic when expanded for the same time period, as shown in FIG. 6. However, Matrigel™-coated surfaces in hyperoxia supported hESC colonies, not EB-like clusters, with near identical morphology to those formed in physiological normoxia.

Characterisation of Pluripotency by Immunoflourescence Staining

Ability of hESCs to retain their pluripotency on PCL nanofibrous substrates (Aligned and random), cultured in 2% $O_2$ for 21 days was investigated by immunoflourescent staining of typical pluripotent gene markers: Alkaline phosphatase (ALP), Nanog and Oct-3/4. As expected, all pluripotent markers (ALP, Nanog and Oct-3/4) were expressed in hESC-CFUs cultured on Matrigel™ substrates (FIGS. 6a, b and c). PCL-Aligned nanofibrous substrates also demonstrated similar expression of ALP, Nanog and Oct-3/4 to Matrigel™ (FIGS. 6d, e and f). PCL-Random nanofibrous substrates also confirmed the pluripotent nature of hESC colonies by the expression of ALP, Nanog and Oct-3/4 with similar expression patterns to hESCs cultured on Matrigel™ (FIGS. 6g, h and i).

Characterisation of Differentiation by RT-PCR

Figure 8:
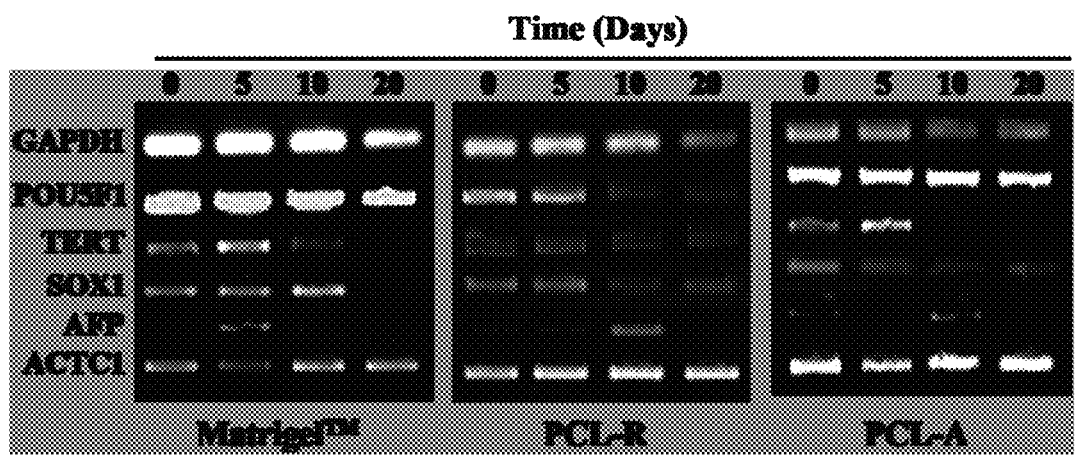
FIG. 8. RT-PCR ran on 2% Agarose Gel electrophoresis to evidently illustrate the presence and expression levels of various genes, on both PCL aligned and random nanofiber substrates including positive control. Qualitative gene expression was investigated at different time points during spontaneous differentiation. Genes investigated include: GAPDH (housekeeping gene), POU5F1 (pluripotent marker), TERT (pluripotent marker) SOX1 (ectoderm germ layer), ACTC1 (mesoderm germ layer) and AFP (endoderm germ layer).

Following recovery hESC colonies on PCL-A and -R in 2% $O_2$ were transferred into spontaneous differentiation media for a further 20 days. Gradual downregulation of POU5F1 and hTERT was immediately apparent on Matrigel-coated and PCL-A coated coverslips and less so on PCL-R (FIG. 8). The retention of a pluripotential differentiation capacity was evidenced by the retention of expression of transcripts associated with the three germ layers; ectoderm (SOX1), endoderm (AFP), and mesoderm (ACTC1). SOX1 and ACTC1 were expressed at similar levels on all scaffold types across the experimental timecourse. AFP expression was generally lost by day 20 during spontaneous differentiation across all three substrates.

Effect of Fiber Diameter on the Expansion of hESCs in Physiological Normoxia

The preferential material for the culture and expansion of hESC colonies with retention of pluripotency and differentiation capacity in 2% $O_2$ was PCL. The fiber diameter of PCL nanofibrous substrates (Aligned and Random) demonstrated strong influence on the expansion of hESC colonies. PCL was electrospun using two polymer concentration solutions; 12.5% and 15%, in both aligned and random conformations. Nanofibers electrospun from these solutions were characterised in terms of fiber morphology, substrate topography and fiber diameter (FIG. 8A). Fiber diameter analysis revealed that 15% PCL solution resulted in nanofibers with a significantly larger diameter in both aligned and random conformations, relative to nanofibers fabricated from 12.5% PCL (FIG. 8B). Hence, 15% PCL nanofibers were denoted as "large" and 12.5% PCL nanofibers were denoted as "small", in both aligned and random conformations, for this section of the study.

PCL nanofibrous substrates with large fiber diameter (aligned and random) and PCL nanofibrous substrates with small fiber diameter (aligned and random) were seeded with hESCs and allowed to expand in 2% $O_2$ for 21 days. As expected, Matrigel™ substrates yielded a significantly greater number of hESC colonies than any nanofibrous substrate (FIG. 8C). Amongst the nanofibrous substrates, the fibers with the overall smallest diameter (PCL-A; 280 nm) significantly supported the greatest number of hESC colonies, relative to any other nanofibrous substrates. The overall schema of colony formation was: Matrigel™, PCL-A (small diameter; 280 nm), PCL-R (small diameter; 318 nm), PCL-A (large diameter; 521 nm) and PCL-R (large diameter; 660 nm). An apparent trend was revealed; with increasing PCL nanofiber diameter; there is a decrease in the number of hESC colony formation. Stained hESC colonies formed on all nanofibrous substrates showed typical hESC colony morphology and displayed distinct similarities amongst each other and Matrigel™ (FIG. 8D).

The integration of nanofiber technology and hESC biology holds great promise for regenerative medicine application. A major hallmark of using nanofibers is that they can be implantable and biodegradable together with the elimination of potential xenocontamination, which accompanies most current and conventional culture of hESCs, providing exciting opportunities for use in clinical therapeutics. Where nanofiber support of hESC culture in vitro has been described, it is reliant on the generation of hybrid polymers or co-culture with a supporting cell layer [30, 31]. This study demonstrates that under physiological oxygen (2% $O_2$) hESCs can adhere to and self-renew on electrospun nanofibrous substrates fabricated from synthetic, FDA approved polymers, without the need for additional substrate support.

hESC attachment and colony formation on electrospun nanofibrous scaffolds was dependant on various conditions, including the use of a reduced, physiological, oxygen culture environment (2% $O_2$), polymer material and fiber diameter. Though the precise mechanisms behind this phenomenon are under current exploration it is important to register that global transcriptome analysis of hESC revealed significant upregulation and downregulation of specific integrin sub-units when cultured in 2% $O_2$, relative to hyperoxic (21% $O_2$) conditions [32]. For instance, integrin sub-units; alpha 6, beta 1, beta 4, alpha E, alpha V, and beta 5 were all expressed at significantly higher levels in physiological normoxia relative to hyperoxia [34-36]. The transcriptional upregulation of integrin subunits associated with laminin (TSP 180 (alpha 6/beta 4), VLA-6 (alpha 6/beta 1), E-cadherin, human mucosal lymphocyte-1 antigen (alpha E), vitronectin (alpha V), and fibronectin (beta 1) binding suggests that nanofiber support of hESC self-renewal could operate through multiple signalling and cell-matrix interaction pathways [34, 35, 37-39]. The expression of specific integrin sub-units between the two oxygen environments could therefore be a determinant of the enhanced adhesion and subsequent self-renewal, which our group, and others, have observed previously in reduced oxygen environments [32, 40, 41]. The inability of hESC cultured in 21% $O_2$ to form self-renewing colonies on nanofiber substrates could also be explained by this model. In this instance the aggregation of hESC into embryoid bodies and subsequent differentiation would induce a hypothetical change in integrin profile to that matched with the nanofiber topography.

Of the polymers tested, PCL supported the recovery of the greatest number of hESC colonies. Colony Size, morphology and differentiation capacity were very similar to those supported on electrospun PCL nanofibers and positive controls. The largest CFU's were observed on Matrigel™-coated and PCL-A nanofiber-coated coverslips. PCL belongs to the aliphatic polyester group of polymers and is considered to be semi-crystalline with resorbable properties permitting a slow degradation rate as a result of its chemically stable and hydrophobic nature [42, 43]. PCL has FDA approval for use in medical devices due to its ready biodegradability into non-toxic by-products and its in vitro and in vivo biocompatibility. Previous cell-based studies have shown that electrospun PCL nanofibrous scaffolds can support numerous cell types including skeletal muscle cells [44], schwann cells [45], fibroblasts [46], bone marrow derived-MSCs [20], human cord-blood derived somatic stem cells [25], mouse ESCs [29] and hESCs [31].

Our results apparently reveal a synergistic effect on hESC colony formation through combining physiological normoxia and nanofiber scaffolds. All reports using nanofiber scaffolds to maintain stemness of human or mouse embryonic stem cells have carried out experiments under hyperoxia conditions with the co-culture of MEFs or, the incorporation of ECM molecules in the nanofiber scaffolds [29, 31]. Without these supporting conditions, naked nanofiber scaffolds alone, under hyperoxic conditions did not support hESC colony formation, which has been confirmed in this study. We hypothesise that under normoxic oxygen environments, hESCs alters their integrin receptor expression pattern as well as the adsorbed proteins from culture media or neo-produced proteins secreted from stem cells themselves that adhere to the nano-scale scaffolds. These factors may play the central role in enhancing stem cell adhesion and self-renewal [47]. It has been reported that selective adsorption of key ECM proteins on nanofibers can alter hESC cytoskeletal morphology on the fibers, consequently resulting in the activation of Rac-AKT-JNK signalling pathways which maintain stem cell pluriopotency [48]. Nanofiber scaffolds have increased surface area for protein attachment in comparison to their bulk-shaped counterpart and can be either hydrophilic or hydrophobic in nature [49]. In this instance the hydrophobic polymer; PCL, supported the largest and greatest number of colonies when compared to the other two polymers investigated. PCL itself displays the greatest degree of hydrophobicity relative to PLGA and PLLA [43]. The alignment and degree of hydrophobicity may therefore be defining characteristics of nanofibers suitable for hESC culture. However it remains necessary to determine the nature of protein adsorption on electrospun nanofibrous scaffolds to fully elucidate their role in the attachment of hESCs.

In addition to the observation that nanofibers could support self-renewal of hESC we also noted that within each specific polymer sub-type a greater number of hESC colonies were recovered on aligned, as opposed to random, nanofibers. Overall PCL-A nanofibers supported the highest number of CFU's, and this lies in agreement with the data demonstrated by our group previously where orientation of electrospun nanofibers improved the isolation efficiency of hMSC colonies, derived directly from bone marrow aspirate [27]. Moreover, CFU's on PCL-A were significantly larger than the other two polymer types. Topography is generally considered to have strong effects on cell activity, as it provides physical guidance, which is able to mimic native fibrillar ECM proteins, a key component of the stem cell niche [50]. Aligned nanofibrous substrates were optimal for both hESC/hMSC adhesion and expansion. An increase in anisotropy is known to increase number of focal adhesion contacts from the cells to the surrounding fibers which may be the reason why aligned nanofibers support larger and greater number of CFU's [13]. Anisotropy has shown to be particularly important during neural stem cell differentiation towards functional nerve cells with increased neurite outgrowth on aligned nanofibers and enhanced differentiation of hMSCs into mesoderm lineages [45, 51]. Here we demonstrate that anisotropy also plays an important role in stimulating cell proliferation of hESCs during culture in physiological normoxia.

Figure 9A:
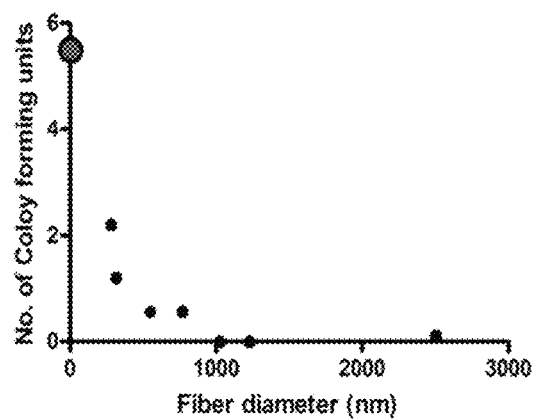
FIG. 9. (A) The fiber diameters of nanofibrous scaffolds as the function of the number of hESC and (B) hMSC colonies formed and their respective colony size when cultured under physiological normoxia. Large dot indicates the value for a Matrigel™-coated control.
Figure 9B:
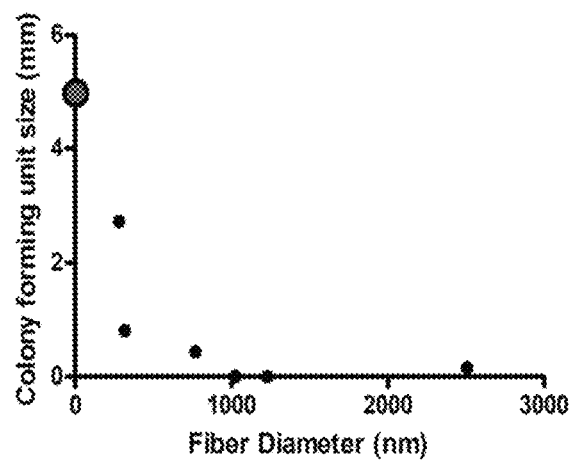
Figure 10:
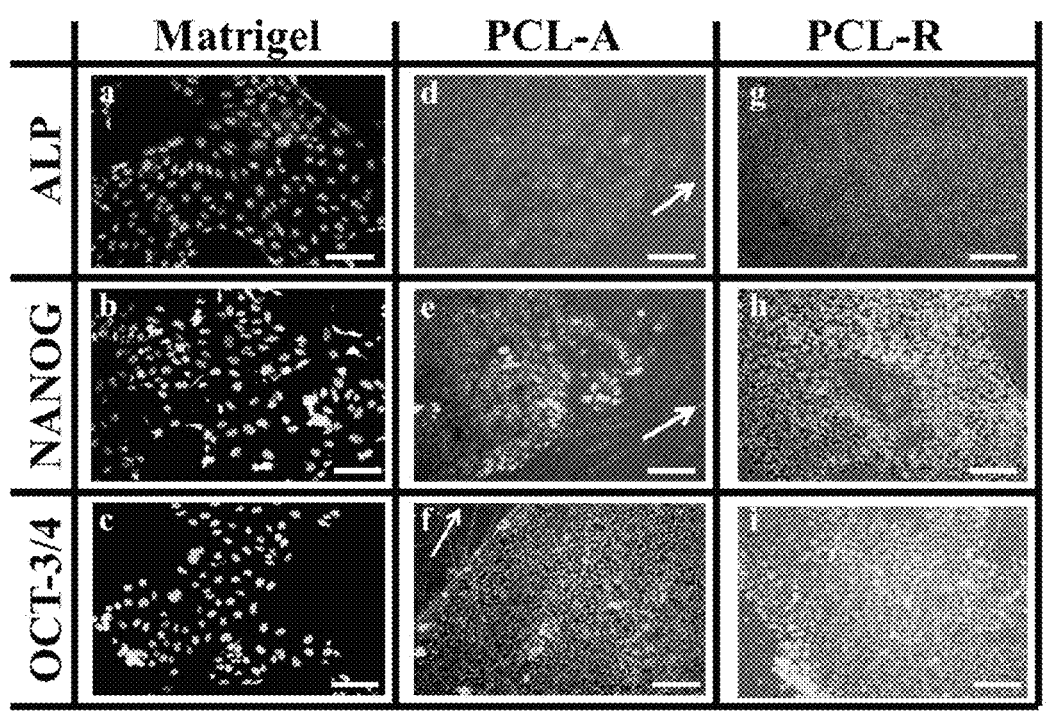
FIG. 10. Immunofluorescent staining of pluripotent marker expression in hESCs cultured on nanofibrous substrates (PCL-A and PCL-R) in physiological normoxia for 21 days. Positive expression of ALP, Nanog and Oct-3/4 in hESCs cultured on: Matrigel™ (a, b and c), PCL-Aligned nanofibrous substrates (d, e and f) and PCL-Random nanofibrous substrates (g, h and i). Scale bar=200 μm.
Figure 11A:
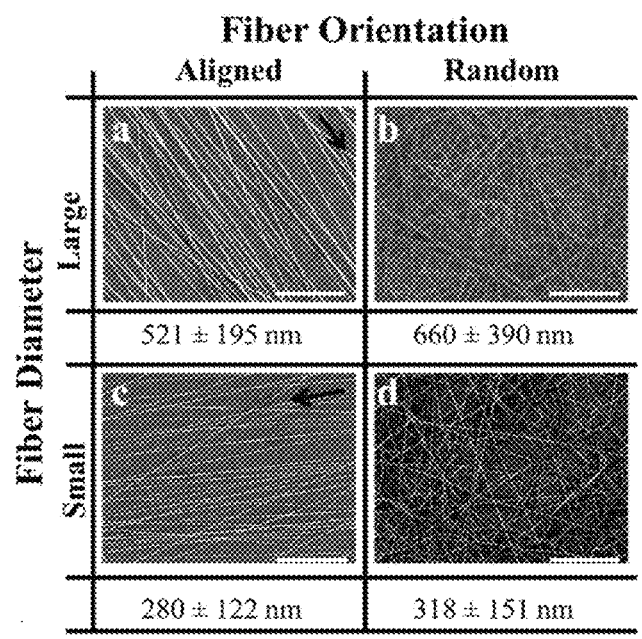
FIG. 11. Relationship between fiber diameter and hESC CFU ability, in physiological normoxia for 21 days. (A) FESEM characterisation of PCL nanofibrous substrates (aligned and random) with large (a and b) and small (c and d) fiber diameters. Nanofiber diameters are presented under each image. An arrow indicates the predominant direction of aligned fibers. Scale bar=3 μm. (B) Average diameters for PCL for both large and small fibers, in both aligned and random conformations. Values indicate mean fiber diameter and standard deviations of n=20; $^a$p<0.05, $^b$p<0.01, $^c$p<0.001. (C) Quantification of formed hESC colonies on PCL nanofibrous substrates with various fiber diameters, in both aligned and random conformations; in physiological normoxia for 21 days. Values indicate mean fiber diameter and standard deviations of n=20; $^a$p<0.05, $^b$p<0.01, $^c$p<0.001. (D) Characterisation of hESC CFU morphology on: (a) Matrigel™⁰, (b) PCL-Aligned with small fiber diameter (280 nm), PCL-Random with small fiber diameter (318 nm), PCL-Aligned with large fiber diameter (521 nm) and PCL-Random with large fiber diameter (660 nm).
Figure 11B:
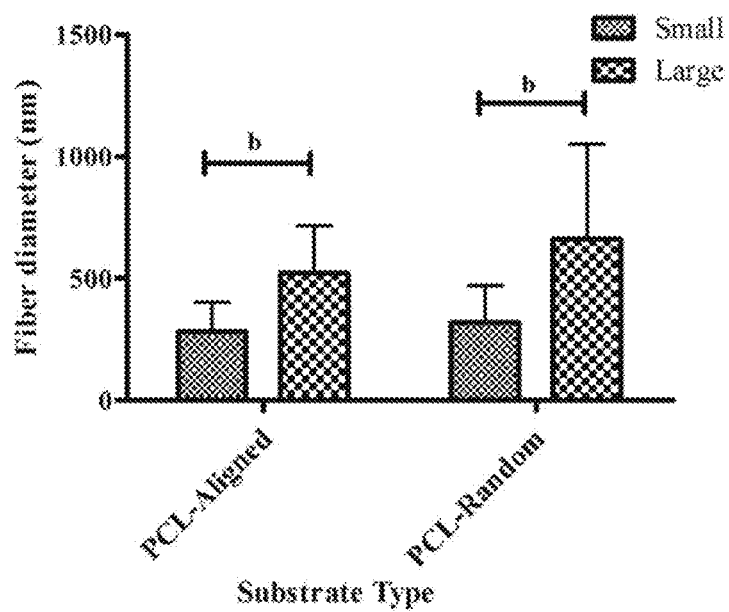
Figure 11C:
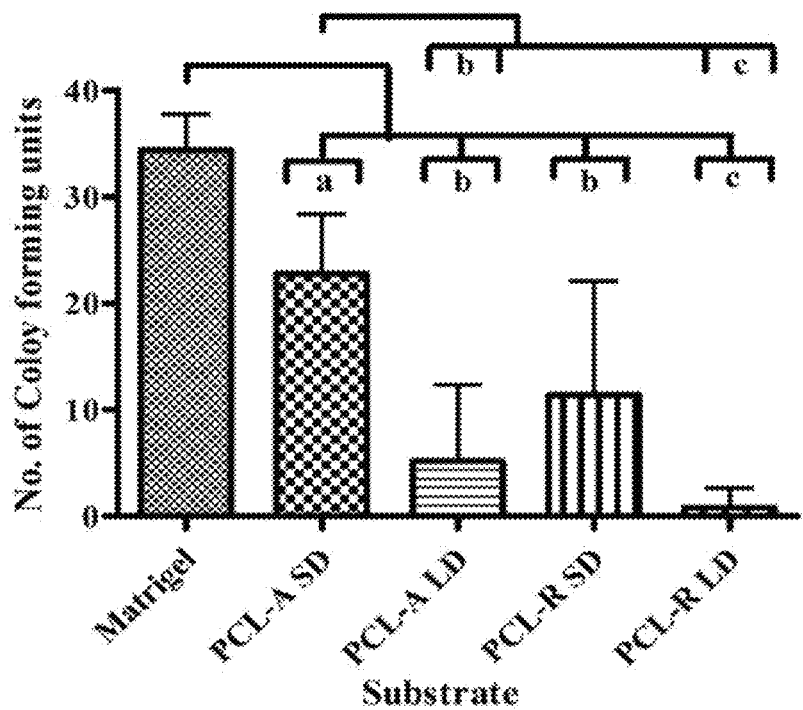
Figure 11D:
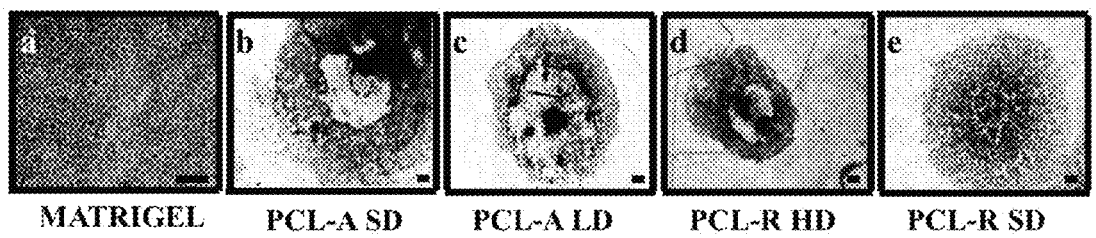

A direct correlation between the CFU size and nanofiber diameter also became apparent (FIG. 9). For example, PCL-A nanofibers have the thinnest fiber diameter (280 nm) but support a greater number of larger CFU's, in contrast to PLLA-A which are the thickest fibers (2506 nm) but yielded the smallest number of CFU's. Furthermore, electrospinning PCL nanofibers at various diameters in both aligned and random nanofibers revealed that smaller diameter nanofibrous substrates (aligned and random) supported significantly a greater number of hESC colonies, relative to their larger diameter counterparts, when expanded in 2% $O_2$. A similar trend was also determined by Wimpenny et al, (2010) using hMSCs where nanofibrous scaffolds fabricated from 0.5% PLGA and 10% PCL had fiber diameters <280 nm but supported the greatest number of colonies in both physiological normoxia and hyperoxia. By combining the data of stem cell (hESC and hMSC) CFU ability and nanofiber diameter (from Wimpenny et al., 2010), a direct correlation was revealed (FIG. 11); this lies in agreement that decreasing fiber diameter results in subsequent increase in the number of CFUs produced with increasing size. These observations have broad agreement across the field where fiber diameters of <500 nm generally promote cell adhesion and encourage greater cell attachment due to increased surface area to volume ratio with an associated increase in the probability of focal adhesion sites available for cell attachment [24, 50]. Our findings are in agreement with this statement, as the largest and the greatest number of CFU's were demonstrated on nanofiber substrates (PCL-A and PCL-R) that had fiber diameters <500 nm. Fiber diameter may therefore play a role of more importance than the chemistry of the polymer itself. The efficiency and size of hESC CFUs may be enhanced for example, by decreasing the fibre diameter of PLGA and PLLA electrospun nanofiber scaffolds used in this study. However, further investigations are required in order to validate this statement.

hESC expansion and differentiation on nanofiber scaffolds realises their use as a non-biological xeno-free substrate with the concurrent elimination of concerns surrounding the transmission of unintentional agents. Successful hESC colony formation and subsequent differentiation is only achievable under physiological normoxia when cultured on naked nanofiber scaffolds. Nanofiber-scaffolds are cost-effective in comparison to conventional methodology and allow themselves readily to high throughput production processes. This encourages further research on hESC culture on synthetic substrates. Though difficult, this will provide novel opportunities for cell therapy and regenerative medicine applications as implantable devices that are biocompatible and biodegradable in vivo.

REFERENCES

1. Burt R K, Loh, Y., Pearce, W., Beohar, N., Barr, W. G., Craig, R., Wen, Y., Rapp, J. A., and Kessler, J. Clinical applications of blood-derived and marrow-derived stem cells for nonmalignant diseases. Journal of American Medical Association 2008; 299(8):925-936.
2. Advanced CT. Advanced Cell Technology Receives FDA Clearance For Clinical Trials Using Embryonic Stem Cells to Treat Age-Related Macular Degeneration; 2011.
3. Alper J. Geron gets green light for human trial of ES cell-derived product. Nat Biotech 2009; 27(3):213-214.
4. Thomson J A, ltskovitz-Eldor, J., Shapiro, S. S., Waknitz, M. A., Swiergiel, J. J., Marshall, V. S., and Jones, J. M. Embryonic stem cells derived from human blastocysts. American association for the advancement of science 1998; 282:1145.
5. O'connor DM, Kardel, M. D., Iosfina, I., Youssef, D., Lu, M., Li, M. M., Vercauteren, S., Nagy, A and Eaves, C. J. Alkaline phosphatase-positive colony formation is a sensitive, specific, and quantitative indicator of undifferentiated human embryonic stem cells. Embryonic stem cells 2004; 26:1109-1116.
6. Xu C, Inokuma, M. S., Denham, J., Golds, K., Kundu, P., Gold, J. D., Carpenter, M. K. Feeder-free growth of undifferentiated human embryonic stem cells. Nature Biotechnology 2001; 19:971-974.
7. Chin-Toh Y, Ng, S., Khong, Y. N., Zhang, X., Zhu, Y., Lin, P. C., Te, C. M., Sun, W and Yu, H. Cellular responses to a nanofibrous environment. Nano Today 2006; 1:34-43.
8. Ma P X, Zhang R. Synthetic nano-scale fibrous extracellular matrix. Journal of Biomedical Materials Research 1999; 46(1):60-72.
9. Tao S L, Desai T A. Aligned Arrays of Biodegradable Poly(îμ-caprolactone) Nanowires and Nanofibers by Template Synthesis. Nano Letters 2007; 7(6):1463-1468.
10. Matthews J A, Wnek, G. E., Simpson, D. G and Bowlin, G. L. Electrospinning of collagen nanofibres. Biomacromolecules 2002; 3:232-238.
11. Zhang Y Z, Venugopal, J., Huang, Z. M., Lim, C. T., and Ramakrishna, S. Characterisation of the surface biocompatibility of the electrospun PCL-collagen nanofibers using fibroblasts. Biomacromolecules 2005; 6:2583-2589.
12. Agarwal S, Wendorff J H, Greiner A. Use of electrospinning technique for biomedical applications. Polymer 2008; 49(26):5603-5621.
13. Yang F, and Murugan, R., Wang, S., and Ramakrishna, S. Electrospinning of nano/micro scale poly(L-lactic acid) aligned fibers and their potential in neural tissue engineering. Biomaterials 2005; 26:2603-2610.
14. Galbraith C G, Sheetz M P. Forces on adhesive contacts affect cell function. Current Opinion in Cell Biology 1998; 10(5):566-571.
15. Jacobson L, Kahan, B., Djamala, A., Thomson, J., and Odorico, J. S. Differentiation of endoderm derivatives, pancreas and intenstine, from rhesus embryonic stem cells. Transplant Proc 2001; 33:674.
16. Kumbar S, James, R., Nukavarapu, S. P., and Laurencin C T. Electrospun nanofibre scaffolds: engineering soft tissues. Biomedical Materials 2008; 3.
17. Sill T J, and Recum, H.A.V. Electrospinning: Applications in drug delivery and tissue engineering. Biomaterials 2008; 29:1989-2006.
18. Teo W, E., and Ramakrishna, S. (2006). A review on electrospinning design and nanofibre assemblies. Nanotechnology 17, R89-R106. A review on electrospinning design and nanofibre assemblies. Nanotechnology. Nanotechnology 2006; 17:R89-R106.
19. Ramakrishna S, Fujihara, K., Teo, W. E., Lim, T. C., and Ma, Z. An introduction to electrospinning and nanofibres. World Scientific Singapore, 2005.
20. Li W, Tuli, R., Huang, X., Laquerriere, P and Tuan, R. S. Multilineage differentiation of human mesenchymal stem cells in a three-dimensional nanofibrous scaffold. Biomaterials 2005; 26(25):5158-5166. Multilineage differentiation of human mesenchymal stem cells in a three-dimensional nanofibrous scaffold. Biomaterials 2005; 25:5158-5166.
21. Bini T, Gao, S., Wang, S., and Ramakrishna, S. Poly(l-lactide-co-glycolide) biodegradable microfibers and electrospun nanofibers for nerve tissue engineering: an in vitro study. Journal of Materials Science 2006; 41:6453-6459.

22. Shih Y R V, Chen, C., Tsai, S., Wang, Y. J and Lee, O. K. Growth of mesenchymal stem cells on electrospun type I collagen nanofibers. Stem Cells 2006; 24:2391-2397.
23. Schnell E, Klinkhammer, K., Balzer, S., Brook, G., Klee, D., Dalton, P., and Mey,
J. Guidance of glial cell migration and axonal growth on electrospun nanofibers of poly-[epsilon]-caprolactone and a collagen/poly-[epsilon]-caprolactone blend. Biomaterials 2007; 28:3012-3025.
24. Ma K, Chan, C. K., Liao, S., Hwang, W. Y. K., Feng, Q and Ramakrishna, S. Electrospun nanofiber scaffolds for rapid and rich capture of bone marrow-derived hematopoietic stem cells. Biomaterials 2008; 29:2096-2103.
25. Hashemi S M, and Soleimani, M., Zargarian, S. S., Hadadi-Asl, V., Ahmadbiegi, N., Solidi, S., Gheisari, Y., Hajarizadeh, A., and Mohammadi, Y. In vitro differentiation of human cord-blood derived unrestricted somatic stem cells into hepatocyte-like cells on poly (ε-caprolactone) nanofiber scaffolds. Cells Tissues Organs 2009; 190: 135-149.
26. Chan C K, Liao, S., Li, B., Lareu, R. R., Larrick, J. W., Ramakrishna, S and Raghunath, M. Early adhesive behavior of bone-marrow-derived mesenchymal stem cells on collagen electrospun fibers. Biomedical Materials 2009; 4:1-10.
27. Wimpenny I, Hampson, K., Yang, Y., Ashammakhi, N., Forsyth, N. R. One-step recovery of marrow stromal cells on nanofibers. Tissue Engineering: Part C 2010; 16(3): 503-509.
28. Yoshimoto H, Shin, M., Terai, H., and Vacanti, J. (2003). A biodegradable nanofiber scaffold by electrospinning and its potential for bone tissue engineering. Biomaterials 24, 2077-2082. A biodegradable nanofiber scaffold by electrospinning and its potential for bone tissue engineering. Biomaterials 2003; 24:2077-2082.
29. Xie J, Willerth, S. M., Li, X., Macewan, M. R., Rader, A., Sakiyama-Elbert, S. E., and Xia, Y. The differentiation of embryonic stem cells seeded on electrospun nanofibers into neural lineages. Biomaterials 2009; 30:354-362.
30. Carlberg B, Axell, M. Z., Nannmark, U., Lui, J., and Kuhn, H. G. Electrospun polyurethane scaffolds for proliferation and neuronal differentiation of human embryonic stem cells. Biomedical Materials 2009; 4:045004.
31. Gauthaman K, Venugopal, J. R., Yee, F. C., Peh, G. S. L., Ramakrishna, S and Bongso, A. Nanofibrous substrates support colony formation and maintain stemness of human embryonic stem cells. Journal of Cell Molecular Medicine 2009; 13:3475-3484.
32. Forsyth N R, Kay, A., Hampson, K., Downing, A., Talbot, R., and McWhir, J. Transcriptome alterations due to physiological normoxic (2% $O_2$) culture of human embryonic stem cells. Regenerative Medicine 2008; 3:817.
33. Rozen S, Skaletsky, H. Primer3 on the WWW for general users and for biologist programmers. Methods in Molecular Biology 2000; 132:365-386.
34. Miyazaki T, Futaki S, Hasegawa K, Kawasaki M, Sanzen N, Hayashi M, et al. Recombinant human laminin isoforms can support the undifferentiated growth of human embryonic stem cells. Biochemical and Biophysical Research Communications 2008; 375(1):27-32.
35. Braam S R, Zeinstra L, Litjens S, Ward-van Oostwaard D, van den Brink S, van Laake L, et al. Recombinant Vitronectin Is a Functionally Defined Substrate That Supports Human Embryonic Stem Cell Self-Renewal via αVβ5 Integrin. STEM CELLS 2008; 26(9):2257-2265.
36. Lee S H, Lee Y J, Han H J. Role of hypoxia-induced fibronectin-integrin β1 expression in embryonic stem cell proliferation and migration: Involvement of PI3K/Akt and FAK. Journal of Cellular Physiology; 226(2):484-493.
37. Wong J C Y, Gao, S. Y., Lees, J. G., Best, M. B., Tuch, B. E. Definitive endoderm derived from human embryonic stem cells highly express the integrin receptors alpha V and beta 5. Cell Adhesion & Migration 2009; 4(1):39-45.
38. Cooper H M, Tamura R N, Quaranta V. The major laminin receptor of mouse embryonic stem cells is a novel isoform of the alpha 6 beta 1 integrin. 1991. p. 843-850.
39. Li L, Wang S, Jezierski A, Moalim-Nour L, Mohib K, Parks R J, et al. A Unique Interplay Between Rap1 and E-Cadherin in the Endocytic Pathway Regulates Self-Renewal of Human Embryonic Stem Cells. STEM CELLS; 28(2):247-257.
40. Ezashi T, Das, P., Roberts, R. M. Low $O_2$ tensions and the prevention of differentiation of hES cells. Proceedings of the National Academy of Sciences of the United States of Amercia 2005; 102:4783-4788.
41. Forsyth N R, Musio, A., Vezzoni, P., Simpson, A. H., Noble, B. S., McWhir, J. Physiologic oxygen enhances human embryonic stem cell clonal recovery and reduces chromosomal abnormalities. Clonal Stem Cells 2006; 8(1):16-23.
42. Barnes C P, Sell S A, Boland E D, Simpson D G, Bowlin G L. Nanofiber technology: Designing the next generation of tissue engineering scaffolds. Advanced Drug Delivery Reviews 2007; 59(14):1413-1433.
43. Kweon H, Yoo M K, Park I K, Kim T H, Lee H C, Lee H-S, et al. A novel degradable polycaprolactone networks for tissue engineering. Biomaterials 2003; 24(5):801-808.
44. Choi J S, Lee, S. J., Christ, G. J., Atala, A., and Yoo, J. J. The influence of electrospun aligned poly(ε-caprolactone)/collagen nanofiber meshes on the formation of self-aligned skeletal muscle myotubes. Biomaterials 2008; 29:2899-2906.
45. Schnell E, Klinkhammer K, Balzer S, Brook G, Klee D, Dalton P, et al. Guidance of glial cell migration and axonal growth on electrospun nanofibers of poly-[epsilon]-caprolactone and a collagen/poly-[epsilon]-caprolactone blend. Biomaterials 2007; 28(19):3012-3025.
46. Chong E J, Phan, T. T., Lim, I. J., Zhang, Y. Z., Bay, B. H., Ramakrishna, S., Lim, C. T. Evaluation of electrospun PCL/gelatin nanofibrous scaffold for wound healing and layered dermal reconstitution. Acta Biomaterialia 2007; 3(3):321-330.
47. Woo K M, Chen V J, Ma P X. Nano-fibrous scaffolding architecture selectively enhances protein adsorption contributing to cell attachment. Journal of Biomedical Materials Research Part A 2003; 67A(2):531-537.
48. Nur-E-Kamal A, Ahmed, I., Kamal, J., Schindler, M., Meiners, S. Three-dimensional nanofibrillar surfaces promote self-renewal in mouse embryonic stem cells. Stem Cells 2006; 24(2):426-433.
49. Wei G, Ma P X. Partially nanofibrous architecture of 3D tissue engineering scaffolds. Biomaterials 2009; 30(32): 6426-6434.
50. Ravichandran R, Liao, S., Ng, C. C. H., Chan, C. K., Raghunath, M., Ramakrishna, S. Effects of nanotopography on stem cell phenotypes. World Journal of Stem Cells 2009; 1(1):55-66.
51. Pittenger M F, Mackay A M, Beck S C, Jaiswal R K, Douglas R, Mosca J D, et al. Multilineage Potential of Adult Human Mesenchymal Stem Cells. 1999. p. 143-147.
51. Dzenis Y Spinning Continuous Fibers for Nanotechnology. Science 2004; 304(5679):1917-1919

52. Li D, Xia Y N. Electrospinning of nanofibers: reinventing the wheel? Adv Mater 2004 16(14)1151-70
53. Ramirez, M. A., Pericuesta, E., Yanez-Mo, M., Palasz, A., and Gutierrez-Adan, A. (2011) Cell prolif. 44: 75-85
54. Ulloa-Montoya, F., Verfaillie, C. M., Hu, W-S (2005) J. Biosci Bioeng 100(1): 12-27

The invention claimed is:

1. A method of culturing human embryonic stem cells (hESC) the method comprising seeding hESC onto an uncoated fiber scaffold in which the fibers are not coated or treated with, and do not incorporate, an extracellular matrix (ECM) component, and wherein the fibers have a diameter of less than about 500 nm, and incubating the hESC loaded fiber scaffold in a gas atmosphere in which the percentage of oxygen is in the range 0.25% to 15%, wherein the cultured hESC maintain stemness.

2. The method of claim 1 wherein the fiber scaffold comprises nanofibers.

3. The method of claim 1 wherein the fiber scaffold comprises electrospun fibers.

4. The method of claim 1 wherein the percentage of oxygen is in the range 0.5% to 10%.

5. The method of claim 1 wherein the percentage of oxygen is about 2%.

6. The method of claim 1 wherein the fibers have a diameter of between 100 nm and 300 nm.

7. The method of claim 1 wherein the fiber scaffold comprises aligned fibers.

8. The method of claim 1 wherein the fibers comprise a synthetic polymer.

9. The method of claim 1 wherein the fibers comprise poly-$\epsilon$-caprolactone (PCL).

10. The method of claim 1 wherein the cultured human embryonic stem cells (hESC) are incubated for 10 days without loss of pluripotency.

11. The method of claim 1 further comprising the step of inducing the cultured human embryonic stem cells (hESC) to differentiate.

12. The method of claim 11 wherein inducing the cultured human embryonic stem cells (hESC) to differentiate comprises adding differentiation media to the fibers seeded with pluripotent stem cells.

13. The method of claim 12 wherein inducing the cultured human embryonic stem cells (hESC) to differentiate comprises removing the pluripotent stem cells from the fibers before adding differentiation medium.

14. A method of preparing a population of human embryonic stem cells (hESC) that are suitable for clinical use comprising expanding a population of hESC by the method of claim 1.

15. The method according to claim 1, wherein the fiber scaffold is, or is connected to an implant.

16. The method of claim 1, further comprising introducing the incubated hESC loaded fiber scaffold to a patient in need of treatment.

17. The method according to claim 1 wherein the percentage of oxygen is in the range 1% to 5%.

* * * * *